United States Patent
Viswanath et al.

(10) Patent No.: US 11,241,190 B2
(45) Date of Patent: Feb. 8, 2022

(54) PREDICTING RESPONSE TO THERAPY FOR ADULT AND PEDIATRIC CROHN'S DISEASE USING RADIOMIC FEATURES OF MESENTERIC FAT REGIONS ON BASELINE MAGNETIC RESONANCE ENTEROGRAPHY

(71) Applicant: Case Western Reserve University, Cleveland, OH (US)

(72) Inventors: Satish Viswanath, Beachwood, OH (US); Iulia Barbur, Akron, OH (US)

(73) Assignee: Case Western Reserve University, Cleveland, OH (US)

(*) Notice: Subject to any disclaimer, the term of this patent is extended or adjusted under 35 U.S.C. 154(b) by 212 days.

(21) Appl. No.: 16/571,454

(22) Filed: Sep. 16, 2019

(65) Prior Publication Data
US 2021/0077009 A1   Mar. 18, 2021

(51) Int. Cl.
*G06K 9/00* (2006.01)
*A61B 5/00* (2006.01)
(Continued)

(52) U.S. Cl.
CPC .......... *A61B 5/4255* (2013.01); *A61B 5/0037* (2013.01); *G06K 9/6231* (2013.01);
(Continued)

(58) Field of Classification Search
CPC ......... G06T 2207/10081; G06T 7/0012; G06T 2207/10088; G06T 7/11; G06T 2207/30004; G06T 2207/30008; G06T 2207/20081; G06T 11/008; G06T 2207/10132; G06T 2207/10072; G06T 2207/10104; G06T 2207/20084; G06T 11/003; G06T 7/12; G06T 2207/10116;
(Continued)

(56) References Cited

U.S. PATENT DOCUMENTS

2017/0193655 A1* 7/2017 Madabhushi ......... G06T 7/0012
2018/0193458 A1* 7/2018 Lopez-Dominguez ....................
C07K 14/4747

OTHER PUBLICATIONS

Wang, An Effective CNN Method for Fully Automated Segmenting Subcutaneous and Visceral Adipose Tissue on CT Scans, Aug. 2019, Biomedical Engineering Society (Year: 2019).*
(Continued)

*Primary Examiner* — Alex Kok S Liew
(74) *Attorney, Agent, or Firm* — Eschweiler & Potashnik, LLC

(57) ABSTRACT

Embodiments discussed herein facilitate predicting response to therapy in Crohn's disease. A first set of embodiments discussed herein relates to accessing a radiological image of a region of tissue demonstrating Crohn's disease associated with a patient; defining a mesenteric fat region by segmenting mesenteric fat represented in the radiological image; extracting a set of radiomic features from the mesenteric fat region; providing the set of radiomic features to a machine learning classifier configured to compute a probability of response to therapy in Crohn's disease based, at least in part, on the set of radiomic features; receiving, from the machine learning classifier, a probability that the region of tissue will respond to therapy; generating a classification of the patient as a responder or non-responder based, at least in part, on the probability; and displaying the classification.

20 Claims, 17 Drawing Sheets

(51) Int. Cl.
*G06T 7/00* (2017.01)
*G06N 20/00* (2019.01)
*G06K 9/62* (2006.01)
*G06N 7/04* (2006.01)
*G06T 7/11* (2017.01)

(52) U.S. Cl.
CPC ........... *G06N 20/00* (2019.01); *G06T 7/0012* (2013.01); *G06N 7/046* (2013.01); *G06T 7/11* (2017.01); *G06T 2207/10088* (2013.01); *G06T 2207/30028* (2013.01)

(58) Field of Classification Search
CPC . G06T 2207/30048; G06T 2207/30096; G06T 2207/30061; G06T 2211/408; G06T 7/0014; G06T 2207/20221; A61B 6/032; A61B 5/055; A61B 6/5217; A61B 6/037; A61B 6/03; A61B 6/5247; A61B 6/482; A61B 6/502; A61B 6/5205; A61B 6/583; A61B 5/0035; A61B 6/504; A61B 6/508
See application file for complete search history.

(56) References Cited

OTHER PUBLICATIONS

Barbur et al. "Automated Segmentation and Radiomic Characterization of Visceral Fat on Bowel MRIs for Crohn's Disease" Proc. of SPIE vol. 10576 1057615-1. Published Mar. 13, 2018.

* cited by examiner

|  | $S_1$ (N = 28) | $S_2$ (N = 44) |
|---|---|---|
| Age | 6 - 21 years | 23 - 76 years |
| Sex | | |
| Male | n = 15 | n = 19 |
| Female | n = 13 | n = 25 |
| Tobacco use history | | n = 11 [Unknown] |
| Yes | N/A | n = 2 |
| No | N/A | n = 9 |
| Growth delay | | |
| Yes | n = 5 | N/A |
| No | n = 16 | N/A |
| Surgical history | n = 0 | n = 20 |
| MR Sequences | Axial HASTE, Axial HASTE SPAIR | Axial HASTE, Axial HASTE SPAIR Trufi, TrufiSP |
| Scanner manufacturer | Siemens | Siemens Phillips |
| Magnetic Field Strength | | |
| 1.5 T | n = 28 | n = 30 |
| 3 T | n = 0 | n = 14 |
| Voxel Spacing (mm) | 0.86 - 1.3 × 0.86 - 1.3 × 3.5 - 5.0 | 0.78 - 1.76 × 0.78 - 1.76 × 4.0 - 7.0 |
| TR/TE (ms) | (389 - 1470) / (67 - 100) | (600 – 1100) / 39 – 80) |

Figure 6

| | MESENTERIC FAT (BPF) (Mean ± SEM) | | | SQF (Mean ± SEM) | | |
|---|---|---|---|---|---|---|
| | Healthy Control | Mild Severity | Moderate Severity | Healthy Control | Mild Severity | Moderate Severity |
| Haralick Energy (ws=5, kurtosis) | 33.43 ± 1.29 | 41.64 ± 4.82 | 71.47 ± 9.43*† | 26.52 ± 3.65 | 32.92 ± 2.64 | 27.09 ± 1.87 |
| Haralick Inertia (ws=3, mean) | 42.15 ± 5.20 | 44.45 ± 5.73 | 102.28 ± 12.00*† | 35.54 ± 3.86 | 34.48 ± 3.14 | 38.26 ± 2.19 |
| Haralick IDM (ws=3, mean) | 0.20 ± 0.01 | 0.21 ± 0.03 | 0.38 ± 0.02* | 0.18 ± 0.02 | 0.16 ± 0.01 | 0.14 ± 0.01 |
| Haralick Sum Average (ws=5, skewness) | 0.33 ± 0.04 | 0.51 ± 0.04 | 0.69 ± 0.07* | 0.39 ± .03 | 0.37 ± 0.03 | 0.36 ± 0.02 |
| L5S5 (ws=3, mean) | 116.15 ± 21.8 | 172.87 ± 20.0 | 284.14 ± 30.3*† | 90.28 ± 4.37 | 99.43 ± 5.96 | 84.91 ± 3.29 |

|  | Predicted Non-responder (%) | Predicted Responder (%) |
|---|---|---|
| Actual Non-responder (%) | TN = 4 (20) | FP = 0 (0) |
| Actual Responder (%) | FN = 3 (15) | TP = 13 (65) |

1410

Feature Predictor
( n = 20 )

|  | Predicted Non-responder (%) | Predicted Responder (%) |
|---|---|---|
| Actual Non-responder (%) | TN = 3 (15) | FP = 2 (10) |
| Actual Responder (%) | FN = 7 (35) | TP = 8 (40) |

1420

Volume Predictor
( n = 20 )

Figure 14

PREDICTING RESPONSE TO THERAPY FOR ADULT AND PEDIATRIC CROHN'S DISEASE USING RADIOMIC FEATURES OF MESENTERIC FAT REGIONS ON BASELINE MAGNETIC RESONANCE ENTEROGRAPHY

FEDERAL FUNDING NOTICE

This invention was made with government support under the grant(s) CA208236 and DK097948 awarded by the National Institutes of Health, and grant(s) W81XWH-16-1-0329 awarded by the Department of Defense. The government has certain rights in the invention.

BACKGROUND

Crohn's disease is a chronic inflammatory bowel disease. Crohn's disease affects an estimated 2.1 million patients in North America and Europe, with approximately two-hundred new cases per 100000 persons each year, of which approximately 25% are pediatric patients. Crohn's disease manifests with a spectrum of activity that can vary on a case-by-case basis, indicating that each patient may require an individualized combination of therapies to ensure optimal outcomes. While a number of existing biomarkers, including eosinophil sedimentation rate, C-reactive protein (CRP), or stool Calprotectin levels, are in routine clinical use, their sensitivity and specificity, even for merely identifying whether Crohn's disease is present, can vary widely. For example, the sensitivity of CRP may range between 49% to 100% for detecting whether a patient has Crohn's disease, while stool Calprotectin has a relatively poor specificity of 43% to 67% for disease diagnosis. Furthermore, existing biomarkers may show elevated levels based on the presence of any inflammatory activity in the human body as a whole, and thus do not provide specific or localized information regarding the activity or severity of Crohn's disease in vivo.

Crohn's disease severity and inflammation may be linked with hypertrophy of visceral adipose tissue (VAT) contained within the abdominal cavity and surrounding the small bowel. Density of mesenteric lymphatic vessels and the presence of B-cell aggregates around these vessels may be associated with a higher risk of post-operative recurrence, and may also be associated with aggressive phenotypes of Crohn's disease. Since the primary modality through which VAT is evaluated in Crohn's disease is imaging, the only existing related markers that are used clinically are volumetric measures, including total VAT volume, and ratio of VAT volume to subcutaneous fat (SQF) volume. While these existing measures have demonstrated specificity of approximately 80% for disease activity, their sensitivity can vary between 40% and 80%, thus limiting their usefulness in clinical situations. Furthermore, existing approaches rely on manual quantification of VAT via computed tomography (CT) imaging, which requires significant expert interaction, or on computationally expensive segmentation techniques. Reliable imaging biomarkers are thus needed to facilitate more accurate therapy selection, better patient management, and improved overall clinical outcomes in Crohn's disease, in both pediatric patients and in adult patients.

BRIEF DESCRIPTION OF THE DRAWINGS

The accompanying drawings, which are incorporated in and constitute a part of the specification, illustrate various example operations, apparatus, methods, and other example embodiments of various aspects discussed herein. It will be appreciated that the illustrated element boundaries (e.g., boxes, groups of boxes, or other shapes) in the figures represent one example of the boundaries. One of ordinary skill in the art will appreciate that, in some examples, one element can be designed as multiple elements or that multiple elements can be designed as one element. In some examples, an element shown as an internal component of another element may be implemented as an external component and vice versa. Furthermore, elements may not be drawn to scale.

FIG. 6 illustrates clinical and imaging characteristics of patient cohorts according to various embodiments discussed herein.

FIG. 10 illustrates radiomic features rank ordered based on p-values from pairwise comparisons between control, mild, and moderate severity groups for mesenteric fat and SQF regions, respectively, according to various embodiments discussed herein.

FIG. 14 illustrates confusion matrices for radiomic predictors and volume predictors according to various embodiments discussed herein.

DETAILED DESCRIPTION

Figure 1:
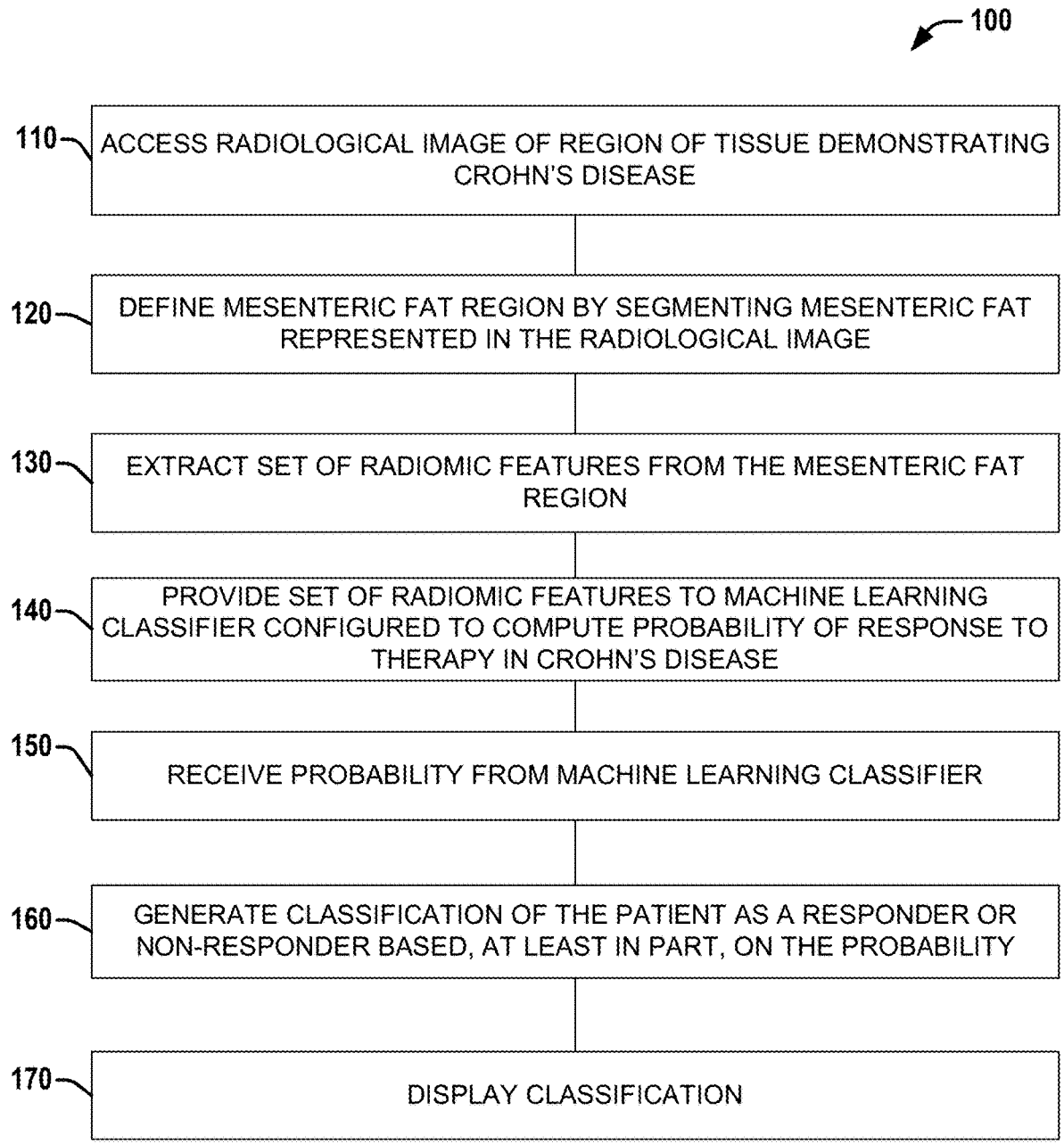
FIG. 1 illustrates a diagram of an example flow of a method or set of operations for predicting response to therapy in Crohn's disease according to various embodiments discussed herein.

Radiomics, including the computerized extraction of quantitative features from medical images, may facilitate more comprehensive Crohn's disease characterization on radiographic imaging compared to existing approaches. Radiomic features may quantify responses to multiple image or mathematical operators applied within local neighborhoods of a region of interest (ROI) on magnetic resonance (MR) or computed tomography (CT) imagery. Embodiments described herein extract radiomic features from mesenteric fat regions, based on a visceral adipose tissue (VAT) region and a subcutaneous fat (SOF) region represented on pre-treatment baseline magnetic resonance enterography (MRE) imagery of a patient demonstrating Crohn's disease. Embodiments quantify sub-visual differences between Crohn's disease phenotypes that may be employed to compute a probability of therapy response in the patient associated with the imagery, or may be employed to classify disease severity. Embodiments facilitate identifying patients, including pediatric Crohn's disease patients or adult Crohn's disease patients, who will or will not respond to therapy for Crohn's disease via baseline, pre-treatment imaging. Embodiments facilitate generation of a non-invasive marker of Crohn's disease activity in vivo, and further facilitate improved therapy selection, improved patient management, as well as improved overall clinical outcomes in Crohn's disease, compared to existing approaches.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic or circuit, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, circuit, processor, or similar electronic device that manipulates and transforms data represented as physical (electronic) quantities.

Example methods and operations may be better appreciated with reference to flow diagrams. While for purposes of simplicity of explanation, the illustrated methodologies and operations are shown and described as a series of blocks, it is to be appreciated that the methodologies and operations are not limited by the order of the blocks, as some blocks can occur in different orders and/or concurrently with other blocks from that shown and described. Moreover, less than all the illustrated blocks may be required to implement an example methodology or operations. Blocks may be combined or separated into multiple components. Furthermore, additional and/or alternative methodologies or operations can employ additional, not illustrated blocks.

Various embodiments can employ techniques discussed herein to facilitate identifying or classifying Crohn's disease patients who will or will not respond to therapy for Crohn's disease via baseline, pre-treatment imaging. Referring to FIG. 1, illustrated is a diagram showing a first example flow of a method or set of operations 100 that facilitates classifying a patient demonstrating Crohn's disease as a responder or non-responder to therapy for Crohn's disease via pre-treatment imaging, according to various embodiments discussed herein. Operations 100 may include acquiring electronic data, reading from a computer file, receiving a computer file, reading from a computer memory, or other computerized activity not practically performed in the human mind.

The set of operations 100 includes, at 110, accessing a radiological image of a region of tissue demonstrating Crohn's disease. The radiological image includes a plurality of pixels, a pixel having an intensity. The radiological image is associated with a patient. In one embodiment, the radiological image is a magnetic resonance enterography (MRE) image or study. The MRE image or study includes a non-fat-suppressed T2w sequence, and a fat-suppressed T2w sequence. In this embodiment, the MRE image is acquired axially to the patient. The radiological image may be a baseline, pre-treatment radiological image or study. Accessing the radiological image may include acquiring electronic data, reading from a computer file, receiving a computer file, reading from a computer memory, or other computerized activity not practically performed in the human mind.

In one embodiment, the MRE image or study includes a plurality of MRI images acquired according to different MRI sequences. For example, a first member of the plurality of MRI images may be acquired according to a first MRI sequence, while a second, different member of the plurality of MRI images may be acquired according to a second, different MRI sequence, while an additional, different member of the plurality of MRI images may be acquired by an additional, different MRI sequence. In one embodiment, where the MRE image or study is associated with a pediatric Crohn's disease patient, the MRE image or study includes an axial HASTE (half-Fourier acquisition single-shot turbo spin echo) MRI image, and an axial HASTE SPAIR (spectral attenuated inversion recovery) MRI image, where the axial HASTE MRI image, and the axial HASTE SPAIR MRI image, each includes a plurality of associated voxels, a voxel having an intensity. In another embodiment, where the MRE image or study is associated with an adult Crohn's disease patient, the MRE image or study includes an axial HASTE MRI image, an axial HASTE SPAIR MRI image, a TruFI MRI image, and a TruFISP MRI image, where the axial HASTE MRI image, the axial HASTE SPAIR MRI image, the TruFI MRI image, and the TruFISP MRI image each includes a plurality of associated voxels, a voxel having an intensity. In another embodiment, other sequences, or combinations of sequences, may be employed.

The set of operations 100 also includes, at 120, defining a mesenteric fat region represented in the radiological image. Defining the mesenteric fat region includes segmenting mesenteric fat or bowel-proximal fat (BPF) represented in the radiological image. Embodiments may automatically segment mesenteric fat represented in the radiological image. In one embodiment, defining the mesenteric fat region includes defining a VAT region by segmenting VAT represented in the radiological image. Defining the mesenteric fat region further includes defining an SQF region by segmenting SQF represented in the radiological image. Defining the mesenteric fat region further includes segmenting mesenteric fat represented in the radiological image based on the VAT region and the SQF region according to techniques described herein. Defining the mesenteric fat region may further include segmenting mesenteric fat represented in the radiological image based on the VAT region, the SQF region, and a proximity to a bowel wall represented in the radiological image. In one embodiment, the proximity to the bowel wall is 5 pixels. In another embodiment, the proximity to the bowel wall may be defined using other, different values, for example, 4 pixels, 6 pixels, 10 pixels, or other, different value. In various embodiments, other, different, automated segmentation techniques may be employed, including for example a connected volume mapping technique, or a clustering and surface fitting segmentation technique. Defining the mesenteric fat region may include acquiring electronic data, reading from a computer file, receiving a computer file, reading from a computer memory, or other computerized activity not practically performed in the human mind.

The set of operations 100 also includes, at 130, extracting a set of radiomic features from the mesenteric fat region. In one embodiment, the set of radiomic features includes at least three radiomic features. Extracting the set of radiomic features includes extracting sub-visual features that are not detectable by the human eye. Extracting the set of radiomic features may include acquiring electronic data, reading from a computer file, receiving a computer file, reading from a computer memory, or other computerized activity not practically performed in the human mind.

In one embodiment, the patient is a pediatric Crohn's disease patient. In this embodiment, the set of radiomic features includes a Gabor feature, a Haralick inverse difference moment (IDM) feature, and a Haralick inertia feature. In this embodiment, the Gabor feature may be a Gabor feature where $\theta=1.9635$, $\lambda=22.6274$, and $p=0.04$. In this embodiment, the Haralick IDM feature may be a Haralick IDM feature where ws=5, and $p=0.05$. In this embodiment, the Haralick inertia feature may be a Haralick inertia feature where ws=3 and $p<0.01$. In another embodiment, the set of radiomic features may include other, different radiomic features.

In one embodiment, the patient is an adult Crohn's disease patient. In this embodiment, the set of radiomic features includes a Laws feature, a Haralick inertia feature, and a Haralick IDM feature. In this embodiment, the Laws feature may be a Laws L5S5 feature where $p=0.02$. In this embodiment, the Haralick inertia feature may be a Haralick inertia feature where ws=3 and $p=0.05$. In this embodiment, the Haralick IDM feature may be a Haralick IDM feature where ws=3 and $p=0.07$. In another embodiment, the set of radiomic features may include other, different radiomic features.

The set of operations 100 also includes, at 140, providing the set of radiomic features to a machine learning classifier. The machine learning classifier is configured to compute a probability of response to therapy in Crohn's disease based, at least in part, on the set of radiomic features. In one embodiment, the computed probability is within the range [0, 1]. In one embodiment, the machine learning classifier is a quadratic discriminant analysis (QDA) classifier. In another embodiment, the machine learning classifier may be another, different type of machine learning classifier, for example, a linear discriminant analysis (LDA) classifier, a support vector machine (SVM) classifier, a random forests (RF) classifier, or a deep-learning classifier, including a convolutional neural network (CNN), configured to compute a probability of response to therapy in Crohn's disease based, at least in part, on the set of radiomic features. Providing the set of radiomic features to the machine learning classifier may include acquiring electronic data, reading from a computer file, receiving a computer file, reading from a computer memory, or other computerized activity not practically performed in the human mind.

The set of operations 100 also includes, at 150, receiving, from the machine learning classifier, a probability that the region of tissue will respond to therapy. The machine learning classifier may compute the probability based, at least in part, on the set of radiomic features. In various embodiments, the probability can comprise one or more of a most likely outcome, for example, as determined based on the set of radiomic features, such as whether a patient is likely to experience response to biologic treatment for Crohn's disease, a probability or confidence associated with a most likely outcome, and/or associated probabilities/confidences associated with each of a plurality of outcomes, for example, response, or non-response. Receiving the probability from the machine learning classifier may include acquiring electronic data, reading from a computer file, receiving a computer file, reading from a computer memory, or other computerized activity not practically performed in the human mind.

The set of operations 100 also includes, at 160, generating a classification of the patient as a responder or non-responder. The classification is generated based, at least in part, on the probability. For example, a first patient associated with a first probability may be classified as a responder, while a second, different patient associated with a second, different probability may be classified as a non-responder. In one embodiment, where the patient is a pediatric Crohn's disease patient, embodiments classify the patient with an AUC of at least $0.79\pm0.09$ for distinguishing responders from non-responders. In another embodiment, where the patient is an adult Crohn's disease patient, embodiments classify the patient with an AUC of at least $0.91\pm0.04$.

The set of operations 100 further includes, at 170, displaying the classification. Operations 100 may, at 170, include displaying the classification and optionally displaying one or more of the radiological image, the mesenteric fat region, the SQF region, the VAT region, the set of radiomic features, or the probability. Displaying the classification and optionally displaying one or more of the radiological image, the mesenteric fat region, the SQF region, the VAT region, the set of radiomic features, or the probability can include displaying the classification and optionally displaying one or more of the radiological image, the mesenteric fat region, the SQF region, the VAT region, the set of radiomic features, or the probability on a computer monitor, a smartphone display, a tablet display, or other displays. Displaying the classification and optionally displaying one or more of the radiological image, the mesenteric fat region, the SQF region, the VAT region, the set of radiomic features, or the probability can also include printing the classification and optionally printing one or more of the radiological image, the mesenteric fat region, the SQF region, the VAT region, the set of radiomic features, or the probability. By displaying the classification and optionally displaying one or more of the radiological image, the mesenteric fat region, the SQF region, the VAT region, the set of radiomic features, or the probability, example embodiments provide a timely and intuitive way for a human medical practitioner to more accurately predict response to therapy in Crohn's disease, or to more accurately classify a patient, thus improving on existing approaches to predicting response to therapy in Crohn's disease. Embodiments may further display operating parameters of the machine learning classifier.

Figure 2:
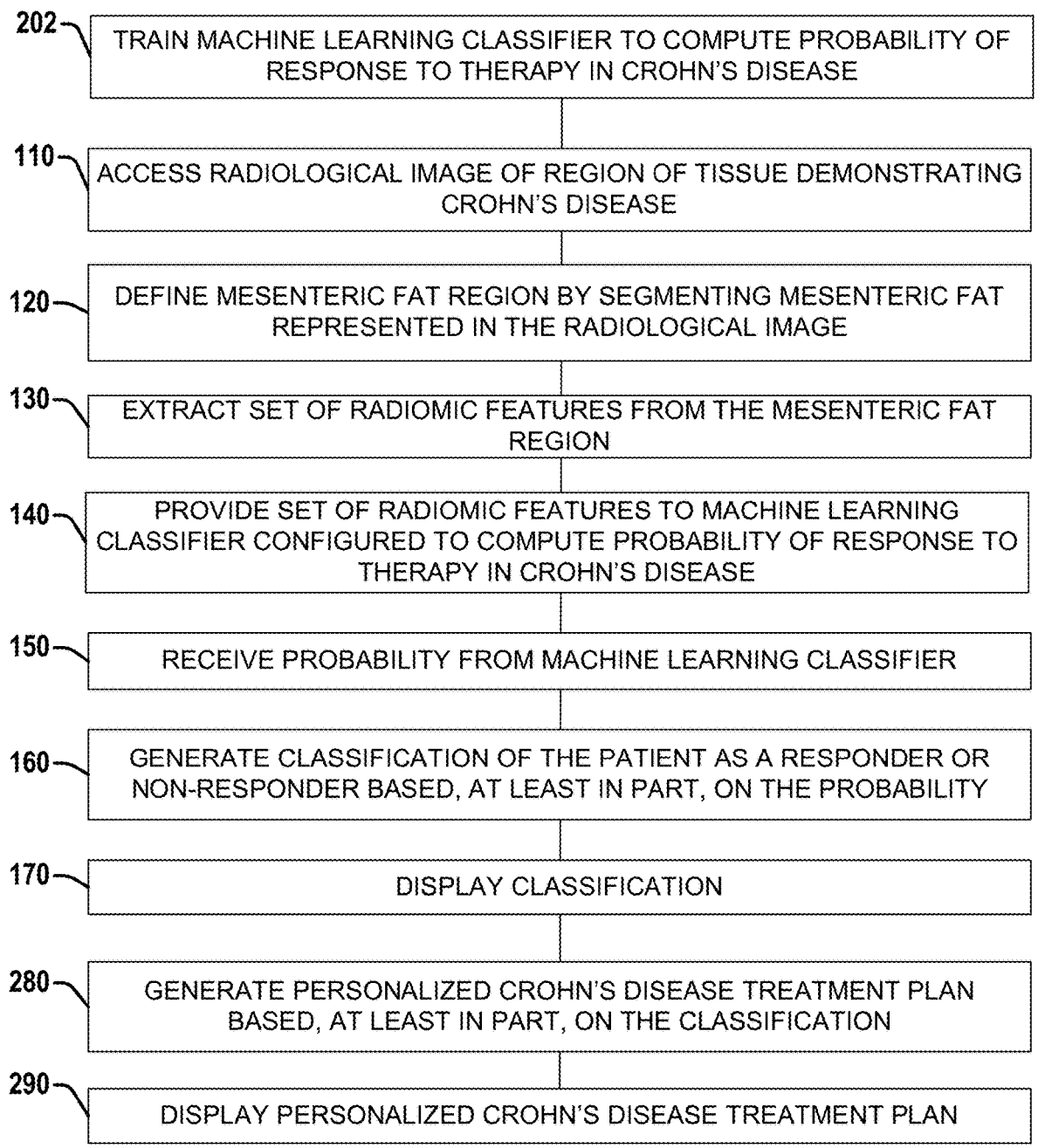
FIG. 2 illustrates a diagram of an example flow of a method or set of operations for predicting response to therapy in Crohn's disease according to various embodiments discussed herein.
Figure 3:
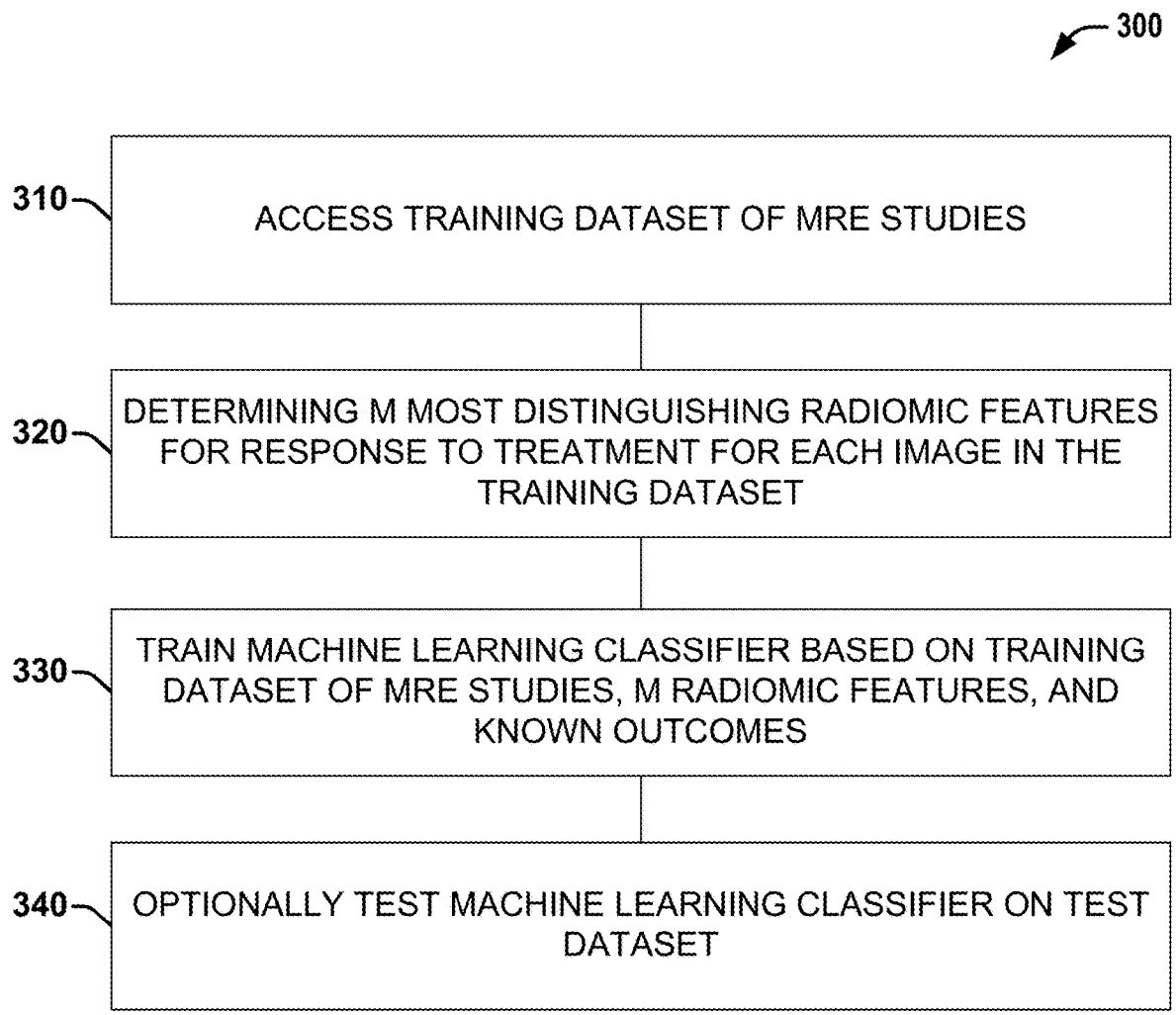
FIG. 3 illustrates a diagram of an example flow of a method or set of operations that facilitates training of a machine learning classifier to generate a probability of response to therapy in Crohn's disease according to various embodiments discussed herein.

FIG. 2 illustrates a set of operations 200 that is similar to operations 100 but that includes additional details and elements. Operations 200 includes, at 202, training the machine learning classifier to compute the probability of response to therapy in Crohn's disease based, at least in part, on the set of radiomic features. FIG. 3 illustrates an example set of operations 300 for training a machine learning classifier to compute the probability of response to therapy in Crohn's disease based, at least in part, on the set of radiomic features according to various embodiments discussed herein.

In one embodiment, the set of operations 300 includes, at 310, accessing a training dataset of MRE studies associated with a plurality of patients demonstrating Crohn's disease. As explained in greater detail herein, the training dataset can comprise a plurality of radiological images, including a positive set that is associated with a first classification (e.g., response to therapy in Crohn's disease) and a negative set that is associated with a different second classification (e.g., non-response to therapy in Crohn's disease). The training dataset includes a plurality of MRE studies comprising a positive set that is associated with a first classification (e.g., responder) and a negative set that is associated with a second, different classification (e.g., non-responder). For example, in this embodiment, at least one member of the plurality of MRE studies is associated with a patient that responded to Crohn's disease therapy, and at least one other, different member of the plurality of MRE studies is associated with a patient that did not respond to Crohn's disease therapy. An MRE study includes a plurality of MRI images, where a member of the plurality of MRI images includes a plurality of associated voxels, a voxel having an intensity. The accessed plurality of MRE studies, or a member of the plurality of MRI images, can be stored in memory locally or remotely, and can be obtained via a medical imaging device one of concurrently with operations 100 or 200 (e.g., via a medical imaging device implementing method or operations 100 or 200) or prior to method or operations 100 or 200. A first member of the plurality of MRI images may be acquired according to a first MRI sequence, while a second, different member of the plurality of MRI images may be acquired according to a second, different MRI sequence, while a third, different member of the plurality of MRI images may be acquired by a third, different MRI sequence. For example, in one embodiment, the MRE study includes an axial HASTE MRI image, and an axial HASTE SPAIR MRI image, where the axial HASTE MRI image, and the axial HASTE SPAIR MRI image, each includes a plurality of associated voxels, a voxel having an intensity. In another embodiment, the MRE study includes an axial HASTE MRI image, an axial HASTE SPAIR MRI image, a TruFI MRI image, and a TruFISP MRI image, where the axial HASTE MRI image, the axial HASTE SPAIR MRI image, the TruFI MRI image, and the TruFISP MRI image each includes a plurality of associated voxels, a voxel having an intensity. While in this embodiment, various MRI sequences are described, in another embodiment, other, different MRI sequences may be employed.

The set of operations 300 can further include, at 320, determining, for each image or MRE study in the training dataset, values for that image for each of the M (where M is a positive integer) most distinguishing radiomic features for response to therapy in Crohn's disease. The M most distinguishing radiomic features can be determined via any of a variety of algorithm or measures including, for example, mRMR, RF, t-test, or Wilcoxon feature selection techniques.

The set of operations 300 can further comprise, at 330, training a machine learning classifier, for example, a QDA classifier, an SVM classifier, and LDA (Linear classifier, a DLDA (Diagonal Line Discriminant Analysis) classifier, an RF classifier, or a CNN classifier, based on the training dataset, and, for each image in the training dataset, the values of the M radiomic features for that image, and a known prognosis (e.g., response to therapy or non-response to therapy in Crohn's disease) associated with that image. Based on the training dataset, and, for each image or MRE study in the training dataset, the values of the M radiographic features for that image, and a known prognosis (e.g., response to therapy or non-response to therapy in Crohn's disease) associated with that image or MRE study, the classifier can determine classes for response or non-response, and probability of response or non-response for associated feature vectors, (e.g., comprising M values of radiomic features).

The set of operations 300 can optionally include, at 340, testing the machine learning classifier on a test dataset comprising radiological images, for example, MRE studies, for which prognoses are known, for example, in a manner similar to set of operations 100 or 200, additionally including comparing a generated prognosis with the known prognosis. In this manner, the ability of the machine learning classifier to correctly classify MRE studies of patients demonstrating Crohn's disease based on response or non-response to therapy can be estimated.

Training the machine learning classifier can also include determining which radiomic features are most discriminative in distinguishing response or non-response to therapy in adult Crohn's disease, or in pediatric Crohn's disease. Training the machine learning classifier can also include determining the optimal combination of operating parameters of the machine learning classifier, or image acquisition parameters, used in the computation of the probability that can best separate a positive class from a negative class (e.g., responders from non-responders, or vice versa).

Returning to FIG. 2, operations 200 also includes, at 280, generating a personalized Crohn's disease treatment plan. The personalized Crohn's disease treatment plan may be generated for the patient. The personalized Crohn's disease treatment plan is based, at least in part, on the classification. In one embodiment, the personalized Crohn's disease treatment plan is further based on the radiological image, or clinical data associated with the patient. Generating the personalized Crohn's disease treatment plan facilitates delivering a particular treatment that will be therapeutically active to the patient, while minimizing negative or adverse effects experienced by the patient. For example, the personalized Crohn's disease treatment plan may suggest a surgical treatment, a monitoring schedule, or may define a therapeutic agent dosage or schedule, when the patient is classified as a responder or likely to experience response to therapy. For a patient classified as a non-responder or unlikely to experience response to therapy, other treatments or schedules may be suggested.

Operations 200 further includes, at 290, optionally displaying the personalized Crohn's disease treatment plan. Displaying the personalized Crohn's disease treatment plan may include displaying the personalized Crohn's disease treatment plan on a computer monitor, a smartphone display, a tablet display, or other displays. Displaying the personalized Crohn's disease treatment plan may also include printing the personalized Crohn's disease treatment plan.

Figure 4:
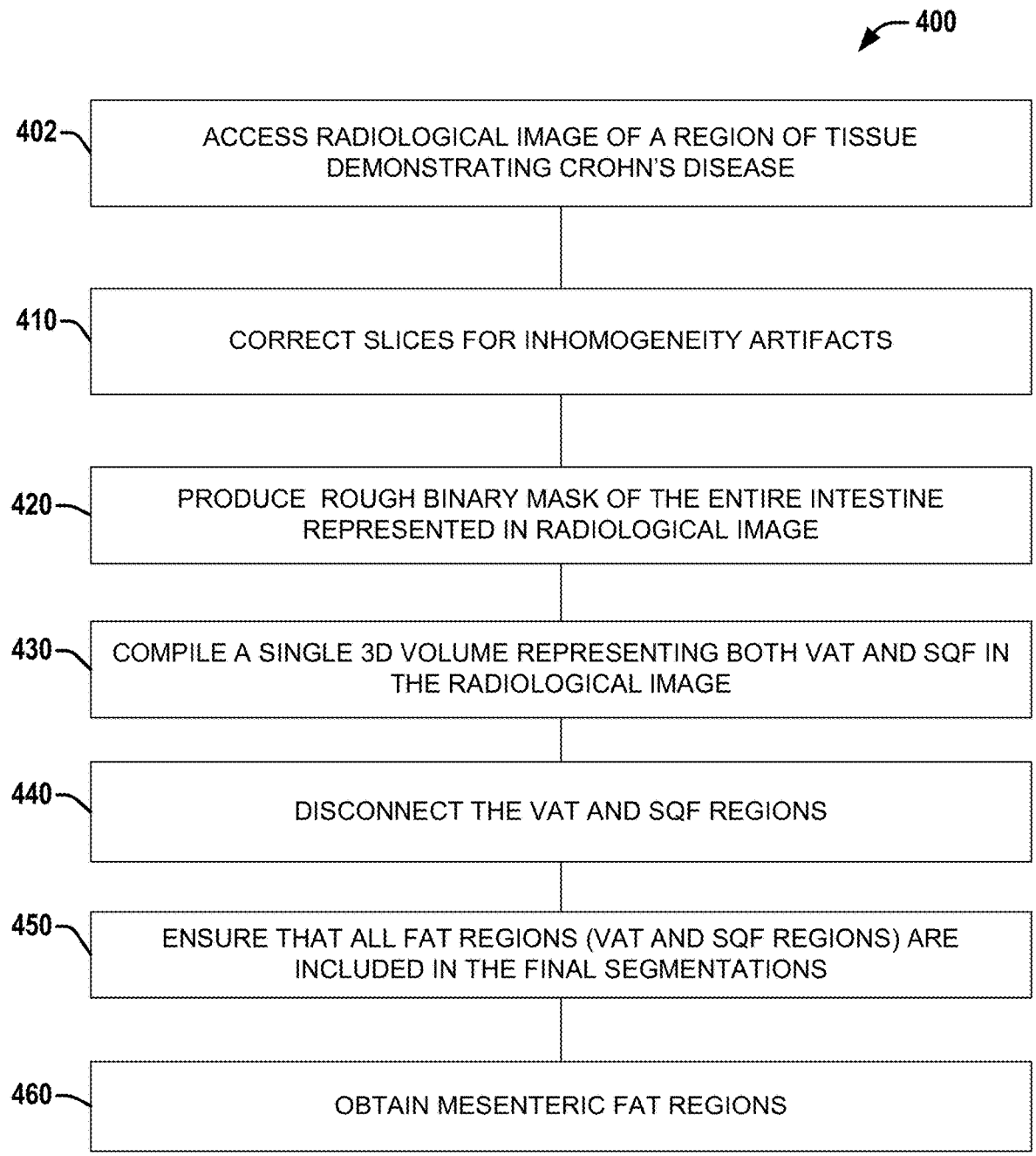
FIG. 4 illustrates a diagram of an example flow of a method or set of operations according to various embodiments discussed herein.

FIG. 4 illustrates an example flow of a method or set of operations 400 that facilitate defining a mesenteric fat region by segmenting mesenteric fat represented in a radiological image. Operations 400 includes acquiring electronic data, reading from a computer file, receiving a computer file, reading from a computer memory, or other computerized activity not practically performed in the human mind. Operations 400 includes, at 402, accessing a radiological image of a region of tissue demonstrating Crohn's disease. In one embodiment, the radiological image may be an MRE study that includes both a non-fat-suppressed T2w sequence, and a fat-suppressed T2w sequence, acquired axially to the patient.

Operations 400 also includes, at 410, correcting slices in both regular (non-fat-suppressed T2w) and fat-suppressed T2w scans for inhomogeneity artifacts.

Inhomogeneity artifacts may manifest as a smooth variation in image brightness across the entire field-of-view. Correcting slices in both regular and fat-suppressed T2w scans for inhomogeneity artifacts may include first estimating the bias field via a low-pass filtering operation, and then removing it from the MRE volume. Correcting slices in both regular and fat-suppressed T2w scans for inhomogeneity artifacts may further include isolating the patient abdomen from background speckle noise via morphological filtering.

Operations 400 also includes, at 420, producing produce a rough binary mask of the intestine. The rough binary mask may be of the entire intestine alone. Producing the rough binary mask includes performing an initial thresholding of the fat-suppressed sequence, which may include a HASTE SPAIR or TRUFISP sequence, to produce a rough intestine mask based on contrast and brightness differences between intestine and other tissue regions, as a result of fat suppression. In this embodiment, the threshold is set at 85 percent of the maximum image brightness for each slice, based on which each two-dimensional (2D) section is thresholded to produce the rough binary mask of the entire intestine alone, denoted $M_{int}$. In another embodiment, the threshold may be set at another, different value, for example, 80 percent, or 90 percent, of the maximum image brightness for each slice.

Operations 400 also includes, at 430 morphologically opening $M_{int}$ using a [3, 3] kernel to produce an intestine mask comprising contiguous regions of bowel. Next, the original 2D MRE image is converted to a binary image, $M_I$ which is then masked by $M_{int}$ to yield $M_{fat}=M_I-(M_I*M_{int})$. This step may then be repeated for every 2D MRE section containing intestinal regions. These 2D $M_{fat}$ are compiled into a single 3D volume, representing all the fat regions (both VAT and SQF) in the MRE scan.

Operations 400 also includes, at 440, disconnecting the VAT and SQF regions. Disconnecting the VAT and SQF regions comprises eroding $M_{fat}$ by a [3, 3] kernel for two iterations to disconnect the VAT and SQF regions. 3D connected component analysis may then be applied to $M_{fat}$, where the largest component corresponds to SQF (denoted $M_{SQF}$) and the second-largest to VAT (denoted $M_{VAT}$). 3D connected component analysis may be employed to identify these regions due to their anatomic characteristics: SQF is typically connected axially, while VAT tends to grow in contiguous segments in Crohn's disease.

Operations 400 also includes, at 450, ensuring that fat regions are included in the final segmentations. Operation 450 may include dilating $M_{VAT}$ and $M_{SQF}$ by a [3, 3] kernel for two iterations, ensuring that all fat regions, or at least a threshold number of fat regions, are included in the final segmentations. Operations 400 may include, at 450, masking the original bias-corrected, noise-reduced T2w scan by M and $M_{VAT}$ to obtain $I_{SQF}$, and $I_{VAT}$.

Operations 400 further includes, at 460, obtaining mesenteric fat or bowel-proximal fat (BPF) regions. Obtaining mesenteric fat regions includes performing further processing on $M_{VAT}$ to obtain the mesenteric fat regions. A mesenteric fat region may include VAT most proximal to the bowel wall itself. In embodiments described herein, the bowel wall may be defined as the outer wall of the small bowel intestinal structure within the body. The bowel wall may be indicated by $M_{int}$. In one embodiment, a mesenteric fat region may include VAT located within five (5) pixels of the bowel wall. In another embodiment, a mesenteric fat region may include VAT located within another, different distance of the bowel wall, for example, 4 pixels, 6 pixels, or other, different distance from the bowel wall. In this embodiment, five slices are selected approximately in the middle of the abdominal cavity, for example between spinal levels L3 and L5, to minimize the presence of muscle and bone in the scan field of view (FOV). For each of these five slices, $M_{int}$ is dilated by a [3, 3] kernel to result in $M_{db}$. Then, regions of mesenteric fat, or BPF, are isolated as $M_{BPF}=M_{VAT}*M_{db}$. $I_{BPF}$ is isolated by masking $I_{VAT}$ by $M_{BPF}$. In another embodiment, another, different number of slices, for example four slices, or six slices, may be selected.

Techniques and aspects of various embodiments are further explained below, in connection with an example embodiment that facilitates predicting response to therapy for an adult Crohn's disease patient or a pediatric Crohn's disease patient, or for classifying a patient as a responder or non-responder in Crohn's disease.

Figure 5:
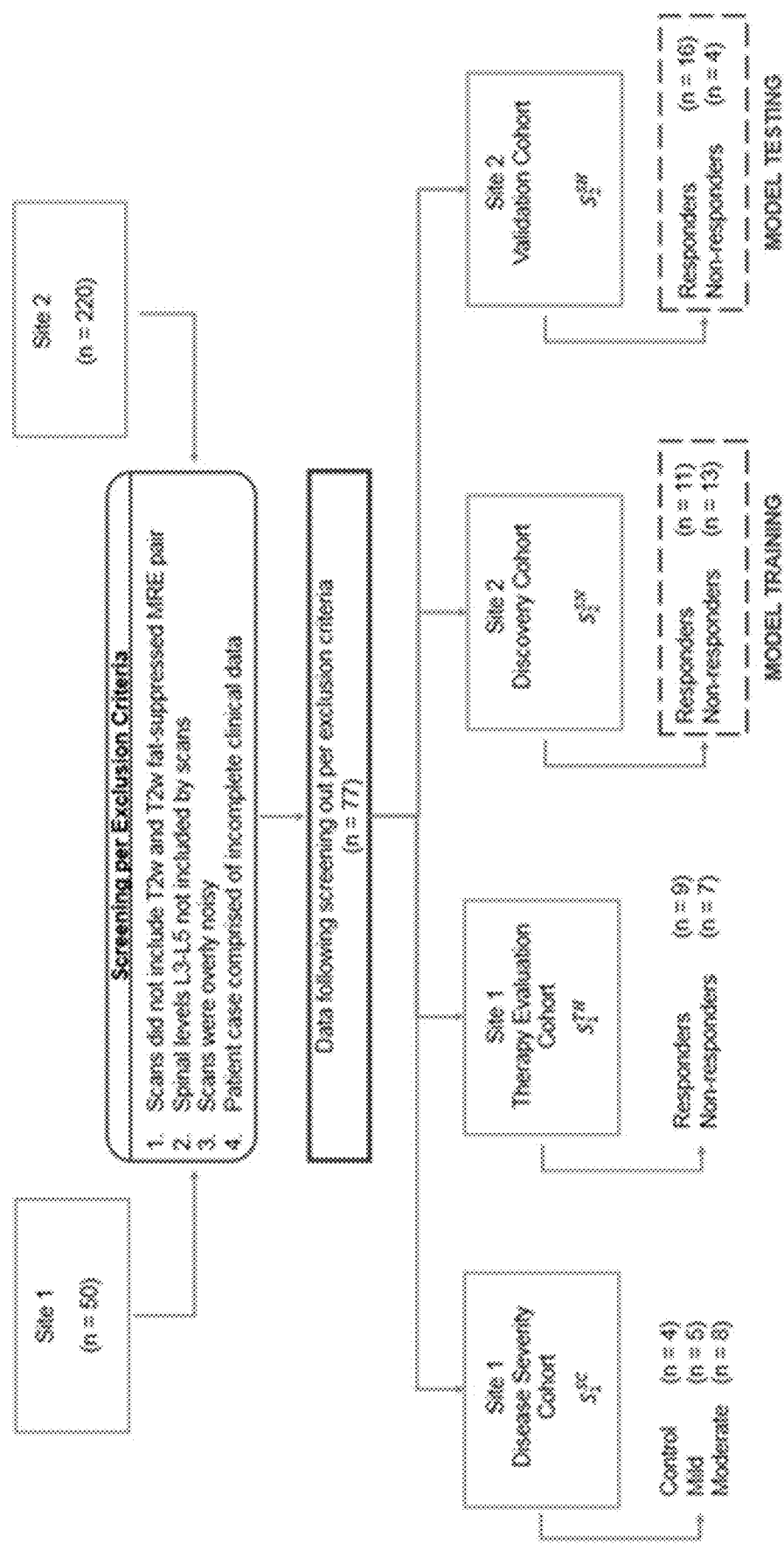
FIG. 5 illustrates a flow chart showing exclusion and inclusion criteria used to curate patient cohorts according to various embodiments discussed herein.

Example Use Case: Radiomic Features of Mesenteric Fat Regions on Baseline Magnetic Resonance Enterography are Predictive of Response to Therapy for Adult and Pediatric Crohn's Disease In one example, imaging and clinical data associated with patients diagnosed with Crohn's disease is collected from two different sites: Site 1, and Site 2. The initial cohort size for Site 1 ($S_1$) was fifty (50) patients, while two-hundred and twenty (220) patients were identified at Site 2 ($S_2$). FIG. 5 illustrates inclusion/exclusion criteria employed in selecting patients at each site, based upon which n=28 patients were curated from $S_1$ and n=44 patients were curated from $S_2$. For all patients included in this example, an MRE study (e.g., scan) was available which included both regular T2w (non-fat suppressed T2w) and fat-suppressed T2w sequences acquired axial to the patient. Clinical and imaging characteristics of the patient cohorts identified at each of Site 1, and Site 2, respectively, are summarized in table 600, illustrated in FIG. 6.

Figure 7:
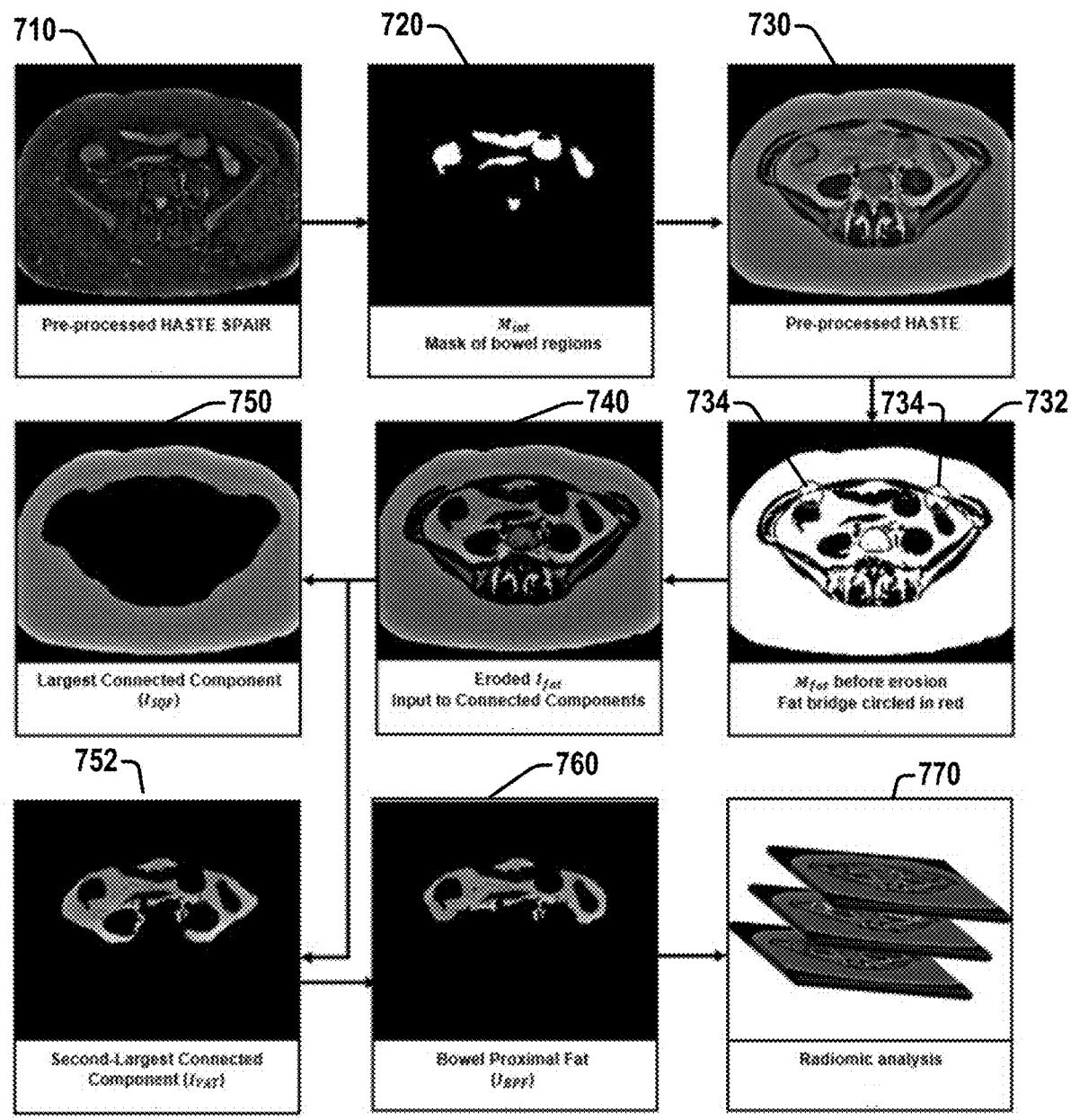
FIG. 7 illustrates a diagram of an example workflow for automated VAT and SQF segmentation according to various embodiments discussed herein.

FIG. 7 illustrates a flowchart of one example overall processing workflow 700 according to various embodiments described herein. Workflow 700 includes steps for automated VAT and SQF segmentation, followed by identification or segmentation of mesenteric fat regions for radiomic analysis. Examples include pre-processing and automatic segmentation of mesenteric or bowel-proximal fat regions on MRI. In one example, an automatic fat segmentation technique is employed to isolate the two fat sub-compartments (VAT, SQF) on abdominal MRE images while optimizing for computational efficiency. Embodiments exploit intrinsic appearance differences between regular (non-fatsuppressed) T2w and fat-suppressed T2w abdominal imaging scans, followed by using anatomic characteristics of the abdominal cavity to identify the VAT and SQF regions. Finally, VAT regions, including mesenteric fat regions, most proximal to the bowel are identified for subsequent radiomic feature extraction and analysis.

Workflow 700 includes, at 710, correcting slices in both regular T2w and fat-suppressed T2w scans for inhomogeneity artifacts, which may manifest as a smooth variation in image brightness across the entire field-of-view. Embodiments may correct slices in both regular T2w and fat-suppressed T2w scans for inhomogeneity artifacts by first estimating the bias field via a low-pass filtering operation, and then removing it from the MRE volume. The patient abdomen is then isolated from background speckle noise via morphological filtering.

Workflow 700 also includes, at 720, performing an initial thresholding of the fat-suppressed sequence, which may include a HASTE SPAIR or TRUFISP sequence, to produce a rough intestine mask based on clear contrast and brightness differences between intestine and other tissue regions, as a result of fat suppression, as illustrated at 710. In this example, the threshold is set at 85 percent of the maximum image brightness for each slice, based on which each 2D section is thresholded to produce a rough binary mask of the entire intestine alone, denoted $M_{int}$, illustrated at 720. The bowel wall may be defined based on $M_{int}$. In another example, the threshold may be set at another, different value.

Workflow 700 also includes morphologically opening $M_{int}$ using a [3, 3] kernel to produce an intestine mask comprising contiguous regions of bowel. Next, the original 2D MRE image, illustrated at 730, is converted to a binary image, $M_I$ which is then masked by $M_{int}$ to yield $M_{fat}=M_I-(M_I*M_{int})$, as shown at 732. This may then be repeated for every 2D MRE section containing intestinal regions. These 2D $M_{fat}$ are compiled into a single 3D volume, representing all the fat regions (both VAT and SQF) in the MRE scan.

VAT and SQF are typically connected via thin fat bridges, highlighted via circles 734 at 732. Workflow 700 also includes eroding $M_{fat}$ by a [3, 3] kernel for two iterations to disconnect the VAT and SQF regions. A representative 2D section from the resulting $I_{fat}$ (after erosion) is illustrated at 740. 3D connected component analysis is then applied to $M_{fat}$, where the largest component corresponded to SQF (denoted $M_{SQF}$) and the second-largest to VAT (denoted $M_{VAT}$). 3D connected component analysis is employed to identify these regions due to their anatomic characteristics: subcutaneous fat is typically always connected axially, while visceral fat tends to grow in contiguous segments in Crohn's disease.

Workflow 700 also includes dilating $M_{VAT}$ and $M_{SQF}$ by a [3, 3] kernel for two iterations, to, in this example, reverse the erosion illustrated at 740, to ensure all fat regions were included in the final segmentations. Finally, the original bias-corrected, noise-reduced T2w scan is masked by $M_{SQF}$ and $M_{VAT}$ to obtain $I_{SQF}$ illustrated at 750, and $I_{VAT}$ illustrated at 752.

Workflow 700 also includes performing further processing on $M_{VAT}$ to obtain mesenteric fat regions, or BPF regions. A mesenteric fat region may include VAT most proximal to the bowel itself. For example, VAT within five pixels of the bowel wall may be included in the mesenteric fat region. In this example, five slices are selected approximately in the middle of the abdominal cavity, for example between spinal levels L3 and L5, to minimize the presence of muscle and bone in the scan FOV. For each of these five slices, $M_{int}$ is dilated by a [3, 3] kernel to result in $M_{db}$. Then, regions of mesenteric fat (e.g., bowel-proximal fat) are isolated as $M_{BPF}=M_{VAT}*M_{db}$. $I_{BPF}$ is isolated by masking $I_{VAT}$ by $M_{BPF}$, illustrated at 760. Radiomic feature extraction from the mesenteric fat region, and analysis, may then be performed at 770, according to various embodiments described herein.

Figure 8:
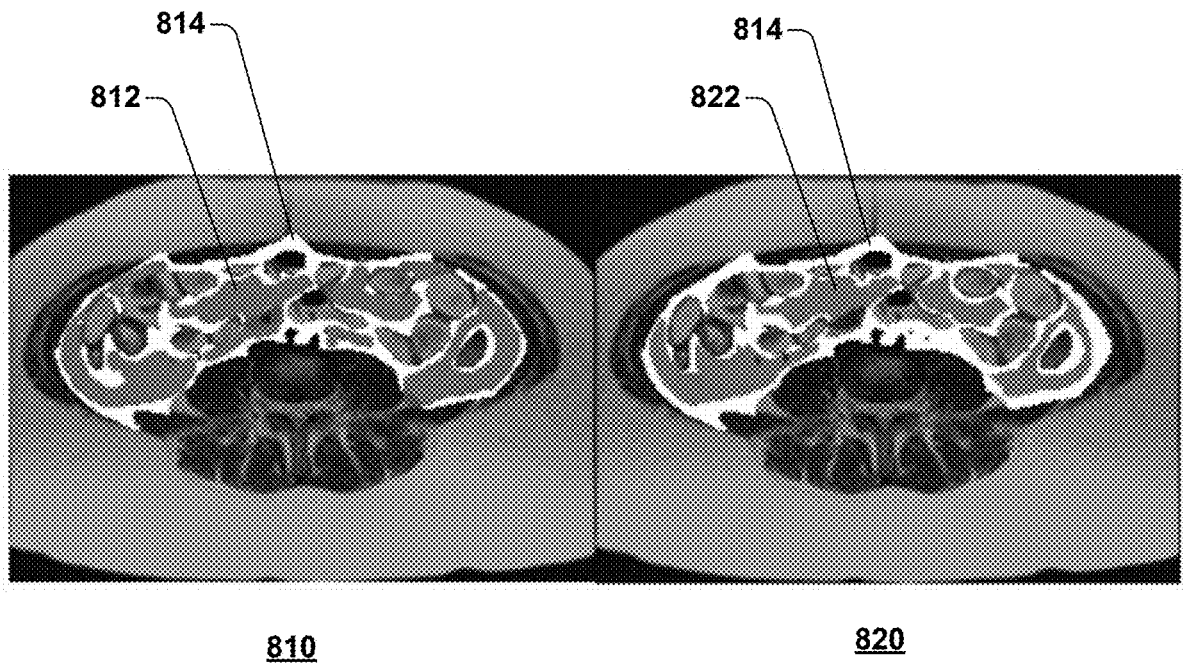
FIG. 8 illustrates representative axial magnetic resonance enterography (MRE) slices according to various embodiments discussed herein.

Embodiments provide improved fat region segmentation compared to existing approaches. In this example, accuracy of the automated fat segmentation scheme was evaluated against expert annotations of the VAT and SQF obtained from two different radiologists, for all MRI datasets in $S_1^{SC}$. Segmentation parameters, including kernel sizes, and threshold levels, were empirically determined using ten sample datasets from $S_1^{SC}$, which were then utilized in the rest of the cohort. Segmentation accuracy was quantified for the two fat regions (VAT, SQF) via the DICE similarity index between (a) the segmentation technique according to various embodiments described herein, and Expert 1, (b) the segmentation technique according to various embodiments described herein and Expert 2, as well as (c) between Expert 1 and Expert 2. FIG. 8 depicts annotations by each of Expert 1 and Expert 2 at 810 and at 820 respectively, overlaid on the segmentation result (in white) at 814. Annotations by Expert 1 are indicated at 812. Annotations by Expert 2 are illustrated at 822.

Figure 9:
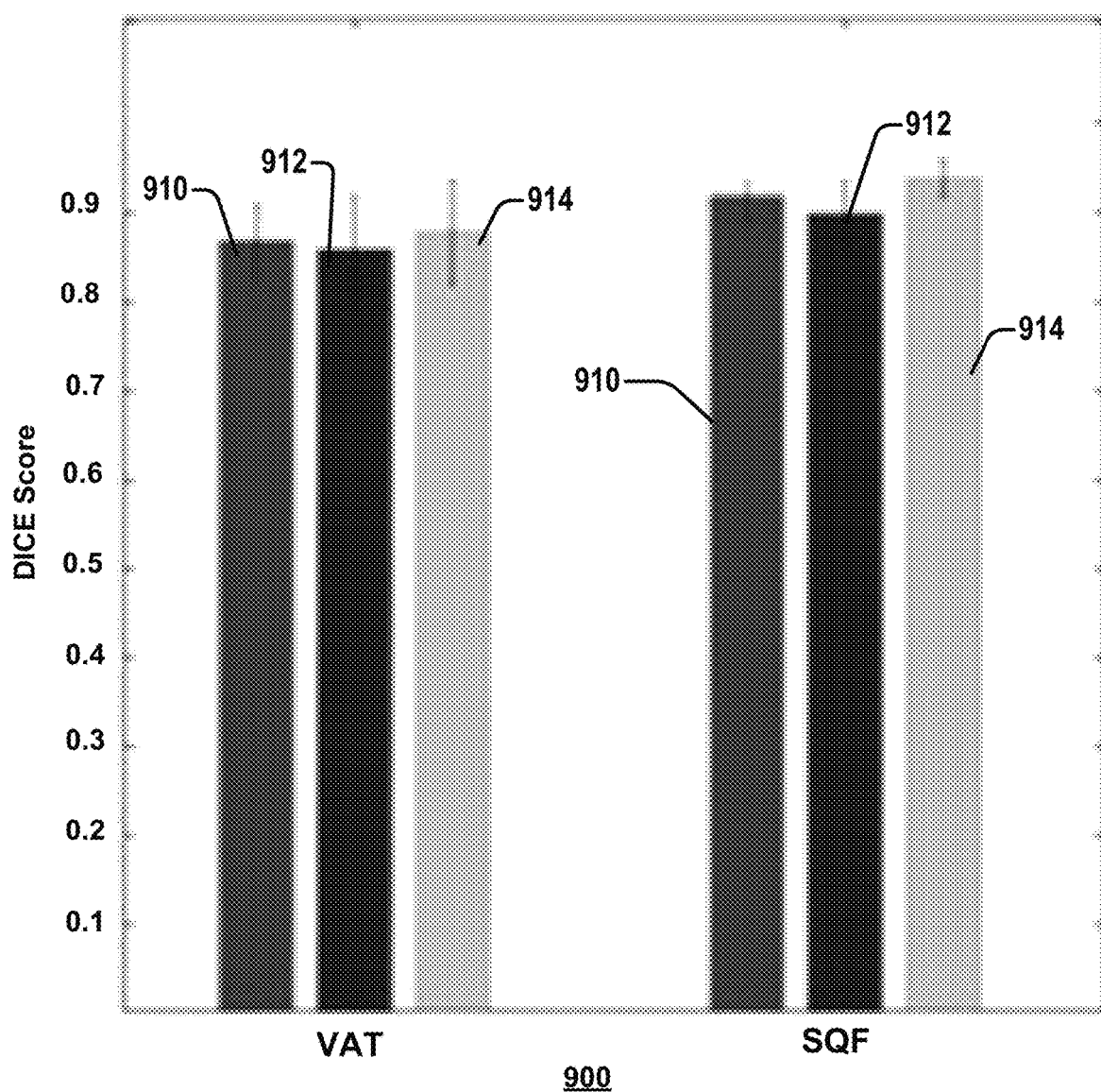
FIG. 9 illustrates a bar plot summarizing DICE scores for segmentation of VAT and SQF regions according to various embodiments discussed herein.

FIG. 9 illustrates a bar chart 900 that summarizes DICE scores between the automated segmentation technique according to various embodiments described herein, compared to the two sets of expert annotations. DICE scores for the segmentation technique described herein vs Expert 1 are illustrated at 910. DICE scores for the segmentation technique described herein vs Expert 2 are illustrated at 912. DICE scores for Expert 1 vs Expert 2 are illustrated at 914. No statistically significant differences in segmentation performance accuracy were observed between the segmentation technique according to various embodiments described herein and the two experts, for either VAT or SQF regions. In this example, a segmentation technique according to various embodiments described herein was used to identify mesenteric fat regions on all 77 patient datasets across $S_1$ and $S_2$ for radiomic analysis, as each member of each dataset had a pair of T2w regular and T2w fat-suppressed scans available respectively.

While some existing segmentation approaches may use manual segmentation, semi-automated segmentation, or fully-automated segmentation techniques for fat identification on MRE, these existing approaches require time and labor intensive activity by human experts, or are computationally expensive, and focus on accurate quantification of VAT and SQF volumes. Embodiments described herein employ an automated segmentation scheme, for example, operations 400 or 700, that efficiently exploits fundamental imaging and anatomic characteristics to extract mesenteric or bowel-proximal fat for radiomic analysis more computationally efficiently than existing approaches. Embodiments, for at least this reason, thus improve the performance of apparatus, systems, processors, computers, or other devices that may implement embodiments described herein.

Embodiments extract radiomic features from the identified mesenteric fat regions represented on MRI. In this example, to capture specific structural and subtle appearance characteristics within mesenteric fat (bowel-proximal fat) on MRI, 147 radiomic features were extracted on a pixel-wise basis from each $I_{BPF}$. These features have physiologic relevance in the current example which is summarized in table 1010 illustrated in FIG. 10. Five statistics, including mean, median, mode, skewness, and kurtosis, of each feature distribution within the mesenteric fat region were utilized in examples described herein, yielding a total of 735 radiomic features.

In this example, based on available clinical and patient outcome data, the 77 patients were grouped as follows: $S_1^{SC}$: n=17 patients from $S_1$ based on short PCDAI scores (38), $S_1^{TH}$: n=16 patients from $S_1$ with therapy outcomes, $S_2^{SN}$: n=24 surgery-naive patients from $S_2$ with therapy outcomes, and $S_2^{SH}$: n=20 surgical history patients from $S_2$ with therapy outcomes.

In this example, for all patients, therapy response was defined based on whether or not patients were recommended for an escalation in therapy within one year following the MRE used for radiomic analysis. In another example, therapy response may be defined using another, different definition, for example, a change in a patient's symptoms based on clinical indices, changes in endoscopic severity, or medical interventions due to Crohn's related complications. In this example, therapy escalation implied either that a change had been administered in medication type or dosage, or that the patient had been recommended for combination of therapy or surgery. In this example, a two-stage feature selection scheme was used to identify a set of mesenteric fat radiomic features that could discriminate between patient groups. First, a pruning step was performed to minimize correlation between features and thus discard non-informative features. Next, minimum redundancy maximum relevancy (mRMR) feature selection was applied to this pruned set of features to retain the subset of the most relevant features that could best differentiate between patient groups. In another example, other feature selection techniques may be employed.

In a first example, based on short PCDAI scores, $S_1^{SC}$ was grouped into healthy controls (n=4), mild disease (10≤PCDAI≤25, n=5), and moderate disease (26≤PCDAI≤40, n=8). Statistical ranksum testing was used to identify which of 735 mesenteric fat or BPF radiomic features demonstrated significant differences in pairwise comparisons between the three PCDAI groups. To test whether radiomic features were being specifically expressed within mesenteric fat regions alone, radiomic features were also extracted from SQF compartments for all patients in $S_1^{SC}$ and tested for being significantly different between the same three groups. The pairwise significance threshold was calculated to be α=0.05/3=0.016, based on applying the Bonferroni correction.

In this first example, a correlation of mesenteric fat radiomic features with pediatric Crohn's disease severity is demonstrated. Table 1010 illustrated in FIG. 10 summarizes the five (5) top-ranked radiomic features (based on p-values against α=0.016 in ranksum testing), as determined via pairwise comparisons of healthy, mild, and moderate disease severity groups in $S_1^{SC}$. Crohn's patients with moderate severity disease are associated with statistically significantly higher mesenteric fat radiomic feature values as compared to healthy controls, as well as when compared to those with mild severity disease. Notably, all five radiomic features were not found to be significantly different within the SQF regions in pairwise comparisons between control, mild, and moderate groups; and only exhibited significant differences within mesenteric fat regions alone. In FIG. 10, * refers to statistical significance when comparing control and moderate disease severity groupings, and † refers to statistical significance when comparing mild and moderate disease severity groupings.

In a second example, based on available outcomes to the baseline therapy administered, $S_1^{TH}$ was grouped into responsive (n=9, did not need therapy escalation) and non-responsive (n=7, required aggressive escalation within 1 year of baseline scan) patients. The three (3) most relevant radiomic features were identified over 25 iterations of threefold cross validation in this cohort, using the 2-stage feature selection scheme described herein. Within each iteration, the top three (3) radiomic features were evaluated using a QDA classifier with the area under the receiver operating characteristic curve (AUC) utilized as a measure of classifier performance (averaged across all cross-validation runs). For comparison, the VAT volume was also computed, based on the results of automated segmentation, and evaluated for how well it could differentiate between the two outcome groups, including cross-validated AUC performance via a QDA classifier. In other examples, other types of classifier described herein may be employed.

Figure 11:
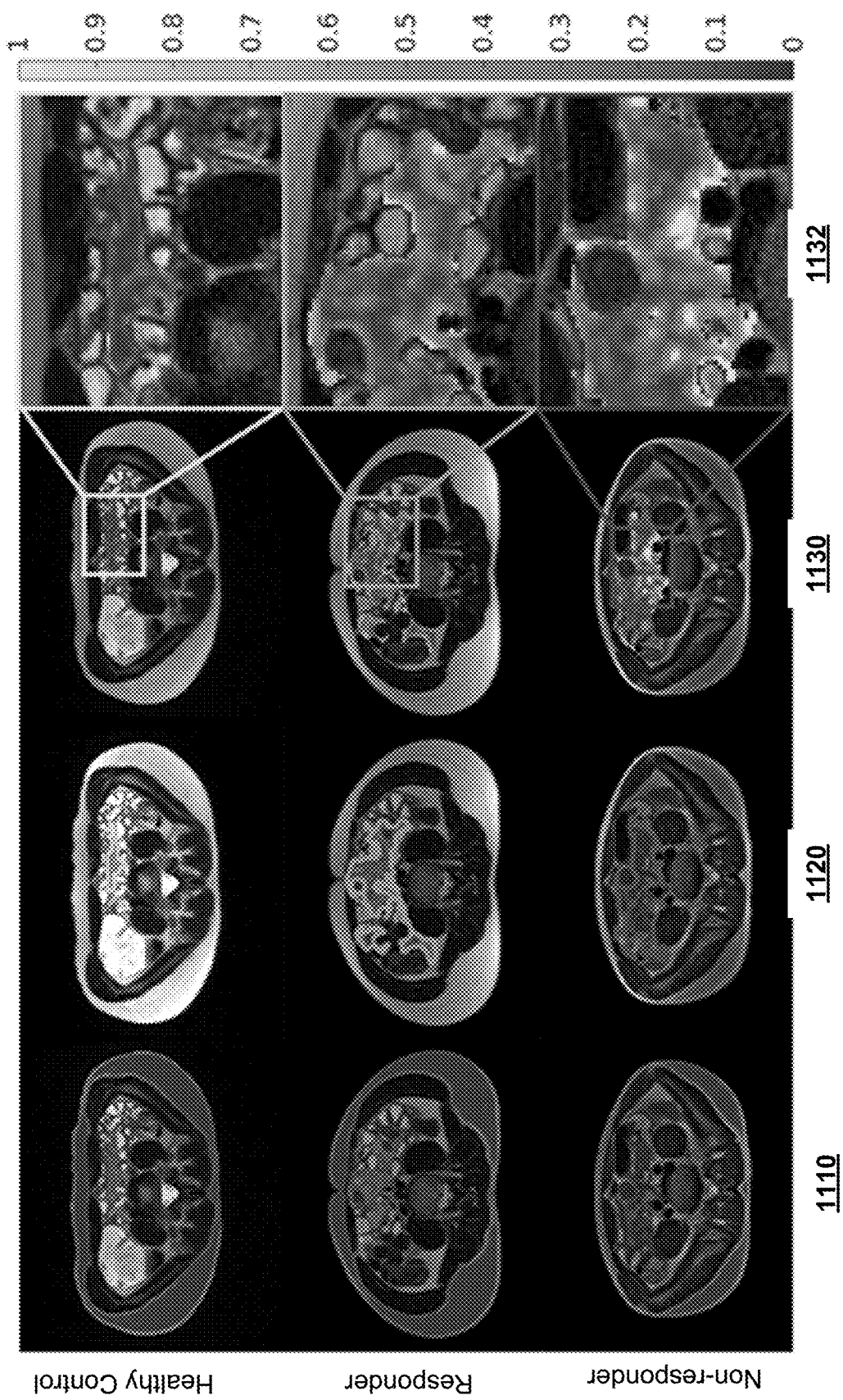
FIG. 11 illustrates representative radiomic heatmap visualizations of a Haralick inertia feature, according to various embodiments discussed herein.

In this second example, radiomic features for predicting response to baseline therapy in pediatric Crohn's disease are evaluated. The three most relevant mesenteric fat radiomic features associated with therapeutic outcomes in $S_1^{TH}$, identified via cross validation, were a Gabor feature (θ=1.9635, λ=22.6274; p=0.04), and two Haralick features (inverse difference moment ws=5, p=0.05, and inertia ws=3, p<0.01). Representative heatmaps for the Haralick inertia feature for a responder, non-responder, and a healthy control patient are illustrated in FIG. 11. FIG. 11 illustrates representative radiomic heatmap visualizations of the Haralick inertia feature (ws=3) with different rows corresponding to different therapeutic outcome groups: non-responder, responder, and healthy control respectively. Different columns in FIG. 11 correspond to radiomic expression within SQF regions at 1110, segmentation outline for the mesenteric fat regions at 1120, and radiomic expression within mesenteric fat regions at 1130. A magnified view of radiomic expression within mesenteric fat regions is illustrated at 1132. Note the relatively homogeneous texture in SQF regions for all three patients at 1110, as well as increasing over-expression of mesenteric fat radiomic features at 1132 across the three rows illustrated in FIG. 11.

In this second example, a progressively higher radiomic expression is observed with increasing disease presence across the three rows illustrated in FIG. 11. This radiomic expression appears specifically within the mesenteric fat regions and not within SQF regions when comparing column 1110 to columns 1130 and 1132. Combining the three (3) top-ranked radiomic features within a QDA classifier resulted in an average cross-validated AUC=0.79±0.09 for distinguishing responders from non-responders in $S_1^{TH}$. By comparison, the VAT volume resulted in a mean AUC of 0.55 (p=0.21).

In a third example, $S_2^{SN}$ was segregated into n=11 responders and n=13 non-responders to biologic therapy, based on available 1-year clinical outcome information. Similar to the second example, the three (3) most relevant features that could best distinguish between the two outcome groups were identified in a cross-validation setting on $S_1^{SN}$, using a two-stage feature selection scheme, with their performance quantified via the average AUC across all cross-validation runs. Radiomic features were then rank-ordered based on their selection frequency across 25 cross-validation runs, in order to pick the most frequently selected descriptors. The top three (3) selected radiomic features were used to train a single QDA classifier on $s_2^{SN}$ to output the likelihood of a patient responding to therapy, employing a range of 0-1. The optimized QDA classifier and associated threshold, to classify a patient as ultimately achieving therapy response, were then evaluated in independent hold-out fashion on $S_2^{SH}$. Validation performance was assessed based on accuracy, specificity, and sensitivity of predicting response to therapy in $S_2^{SH}$. A VAT volume-based predictor was similarly evaluated for the same task, using $s_2^{SN}$ and $S_2^{SH}$ as described herein.

In this third example, radiomic features for predicting response to biologic therapy in adult Crohn's disease are evaluated. In this example, the three (3) top-selected radiomic features in distinguishing between the two outcome groups in the discovery cohort $S_2^{SN}$ were a Laws feature (L5S5, p=0.02), Haralick inertia (ws=3, p=0.05), and Haralick IDM (ws=3, p=0.07). The former two features are depicted as radiomic heatmaps for representative responder and non-responder cases from each of the discovery ($S_2^{SN}$) and validation ($S_2^{SH}$) cohorts in FIG. 12, revealing markedly higher heterogeneity (lighter, yellow regions) in mesenteric fat regions in non-responder patients. Training a QDA classifier to distinguish between response groups in $S_2^{SN}$ using the top three radiomic features according to embodiments described herein resulted in average cross-validated AUC of 0.91±0.04, illustrated by curve 1320 in FIG. 13. By comparison, a QDA classifier trained on volume features (VAT, SQF, and VAT:SQF ratio) according to existing approaches, resulted in a significantly lower AUC=0.57±0.09, illustrated by curve 1330 in FIG. 13, where p<0.001. Hold-out validation of the radiomic predictor on $S_2^{SH}$ according to embodiments described herein yielded an overall accuracy of 0.85, which was markedly higher than the volume predictor (accuracy=0.60) according to existing approaches.

Figure 12:
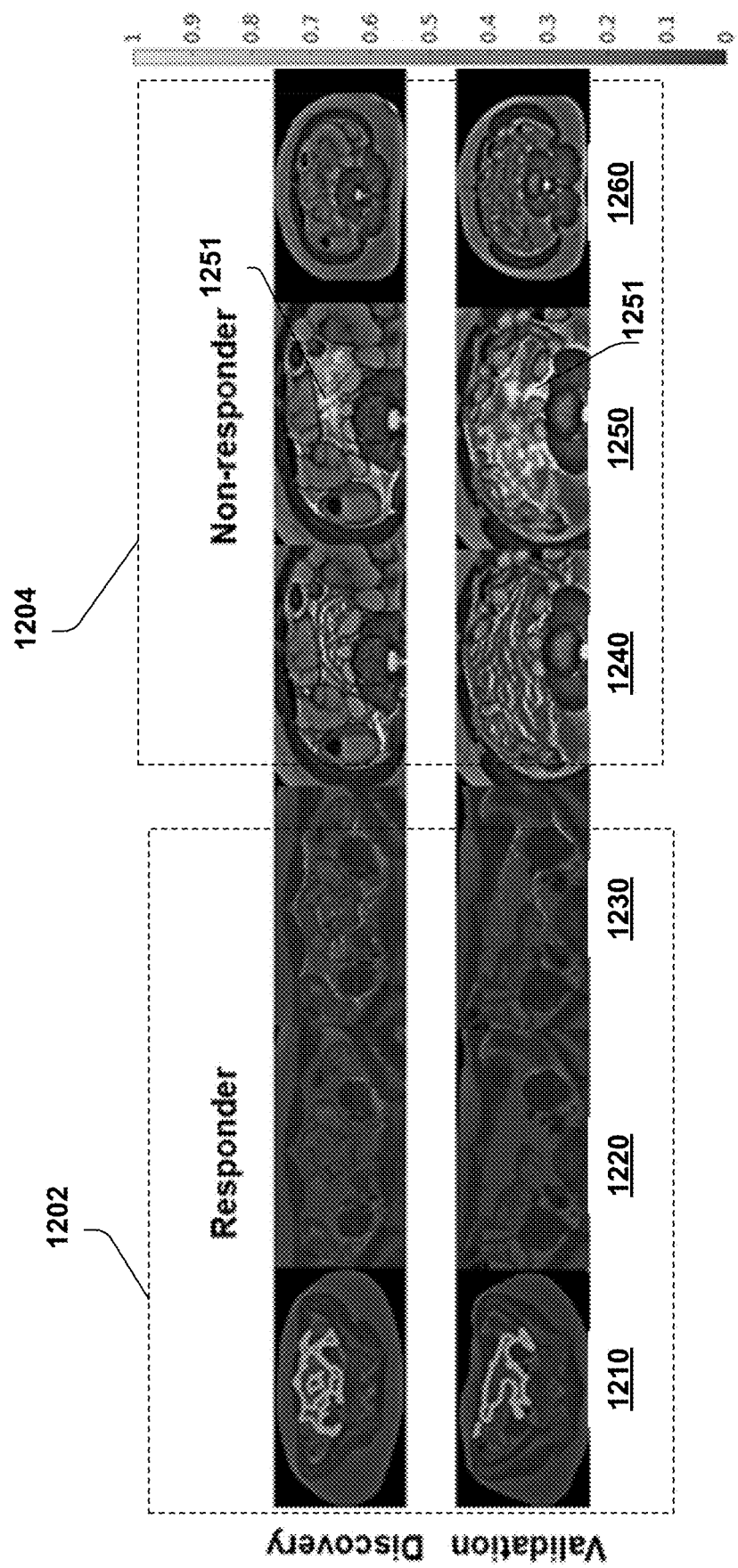
FIG. 12 illustrates representative radiomic heatmaps for responders and non-responders according to various embodiments discussed herein.

Referring to FIG. 12, representative radiomic heatmaps for responders 1202 (left) and non-responders 1204 (right), from the discovery ($S_2^{SN}$) and validation ($S_2^{SH}$) cohorts are illustrated. In FIG. 12, columns 1210 and 1260 correspond to mesenteric fat (BPF) segmentation outlines, columns 1220 and 1250 correspond to a Haralick inertia (ws=3) heatmap, and columns 1230 and 1240 correspond to a Laws L5S5 heatmap. Note the significantly more heterogeneity and over-expression of radiomic features, including more fluctuations and lighter yellow regions 1251, in non-responders 1204 compared to responders 1202; a trend which is consistent between the discovery cohort (top row) and validation cohort (bottom row).

Figure 13:
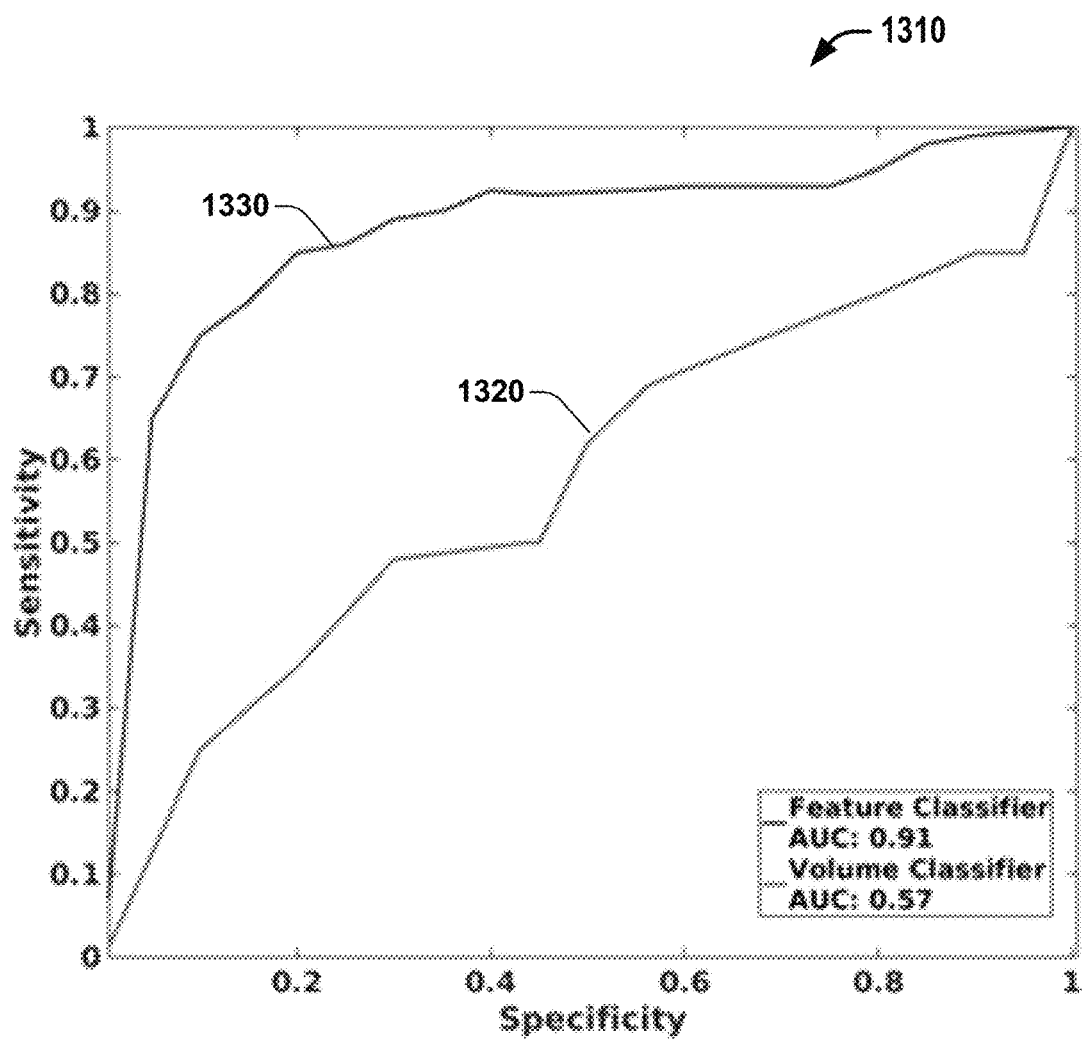
FIG. 13 illustrates receiver operating curves (ROC) for radiomic predictors and volume predictors according to various embodiments discussed herein.

Referring to FIG. 13, graph 1310 illustrates an ROC 1330 for the radiomic predictor according to embodiments described herein, and an ROC 1320 for a volume predictor based on cross-validation in the discovery cohort ($S_2^{SN}$). FIG. 14 illustrates confusion matrix 1410 for the radiomic predictor according to embodiments, and also confusion matrix 1420 for the volume predictor; both based on hold-out evaluation on $S_2^{SH}$.

There is a significant clinical need to accurately predict whether a Crohn's disease patient will respond to aggressive treatment or not. Existing biomarkers of intestinal inflammation such as CRP, ESR, and stool Calprotectin are not always both specific and sensitive with regards to the extent and severity of overall inflammation in the gastrointestinal tract. Embodiments described herein employ radiomic features extracted from 3D imaging to non-invasively visualize the presence and extent of Crohn's disease in vivo, and thus facilitate better guided treatment decisions, and thus improved patient outcomes compared to existing approaches.

Embodiments described herein extract and evaluate radiomic features from the visceral, mesenteric fat in patients with Crohn's disease, capturing more advanced, and more discriminative, appearance and texture characteristics of these regions on imaging compared to existing approaches. Across two different sites involving populations of adult and pediatric Crohn's disease, radiomic features according to embodiments described herein specifically over-expressed within regions of mesenteric fat in diseased patients, and may be used to differentiate between disease severity as well as therapy outcome groups with greater accuracy and specificity than existing approaches.

Mesenteric fat regions segmented and represented on 3D pathology imagery according to various embodiments described herein exhibit more heterogeneous texture appearance in patients with moderate Crohn's disease, in whom all five of the top-ranked radiomic features exhibit significantly higher values compared to healthy controls as well as mild severity disease. Embodiments described herein demonstrate that over-expression of radiomic heterogeneity in mesenteric fat is correlated with more severe disease and may therefore be driven by the effects of Crohn's disease in these patients.

Radiomic features extracted from mesenteric fat regions according to embodiments described herein also more accurately distinguish between responders and non-responders to therapy across cohorts of adult and pediatric Crohn's disease patients, and more accurately predict response from baseline imagery compared to existing approaches. Notably, two of the top-ranked features from the first example, including Haralick inertia and Haralick IDM, which capture turbulence or smoothness of image appearance, exhibit significant differences between therapy outcomes to baseline, in children, as well as aggressive biologic therapy in adults, for Crohn's disease.

Despite the adult and pediatric cohorts being highly heterogeneous, having been accrued retrospectively from different sites, different patient populations, different scanner strengths, and from scanners from different manufacturers, similar mesenteric fat radiomic features were independently identified in each of them, with two features in common between the second example and the third example. In addition to reinforcing observations that mesenteric fat radiomic features may be closely linked to Crohn's disease phenotypes, these features are relatively reproducible across site and scanner differences according to various embodiments described herein. Notably, existing volume-based measures of the visceral fat resulted in significantly poorer predictive performance in distinguishing therapeutic outcome groups for Crohn's disease. In contrast, embodiments described herein employing mesenteric fat radiomic features demonstrate higher predictive accuracy for differentiating disease outcomes, including in limited hold-out validation, indicating that embodiments provide more sensitive and more specific markers of Crohn's disease than existing approaches.

Existing approaches to distinguishing phenotypes in Crohn's disease have focused on quantifying bowel motility, automatically segmenting diseased bowel locations, or characterizing the appearance of the inflamed bowel wall alone. Some existing approaches report that texture features within inflamed bowel wall locations on MRI differ based on presence of hypoxia or angiogenesis or as a result of histological disease activity differences. In contrast, embodiments described herein evaluate radiomic texture signatures within automatically segmented mesenteric fat regions for their connection both to Crohn's disease severity as well as therapy outcomes. Examples described herein use one of the largest cohorts to be evaluated for computational approaches in Crohn's disease (N=77 from 2 sites compared to max N=49 thus far in existing approaches). Further, embodiments employ radiomic features across both adult and pediatric populations, and include hold-out validation of the resulting predictor, resulting in increased confidence compared to existing approaches.

In various example embodiments, method(s) or operations discussed herein can be implemented as computer executable instructions. Thus, in various embodiments, a computer-readable storage device can store computer executable instructions that, when executed by a machine, for example a computer or processor, cause the machine to perform methods or operations described or claimed herein including operation(s) described in connection with methods or operations 100, 200, 300, 400, or 1700, or any other methods or operations described herein. While executable instructions associated with the listed methods or operations are described as being stored on a computer-readable storage device, it is to be appreciated that executable instructions associated with other example methods or operations described or claimed herein can also be stored on a computer-readable storage device. In different embodiments, the example methods or operations described herein can be triggered in different ways. In one embodiment, a method or operation can be triggered manually by a user. In another example, a method or operation can be triggered automatically.

Embodiments discussed herein related to predicting pediatric or adult Crohn's disease patient response to therapy, classifying a pediatric Crohn's disease patient or adult Crohn's disease patient as a responder or non-responder, analyzing Crohn's disease severity, training a machine learning classifier to predict a pediatric or adult Crohn's disease patient response to therapy, or determining a probability that a patient will respond or not respond to Crohn's disease therapy, are based on features that are not perceivable by the human eye, and their computation cannot be practically performed in the human mind. An MRE study including a plurality of MRI scans acquired according to different sequences as described herein cannot be implemented in the human mind or with pencil and paper, for at least the reason that a human mind cannot perform or store an MRE study of a human bowel. Embodiments thus perform actions, steps, processes, or other actions that are not practically performed in the human mind, at least because they require a processor or circuitry to access digitized images stored in a computer memory and to extract or compute features that are based on the digitized images and not on properties of tissue or the images that are perceivable by the human eye. Embodiments described herein can use a combined order of specific rules, elements, operations, or components that render information into a specific format that can then be used and applied to create desired results more accurately, more consistently, and with greater reliability than existing approaches, thereby producing the technical effect of improving the performance, including at least the predictive accuracy or the computational efficiency, of the machine, computer, or system with which embodiments are implemented.

Figure 15:
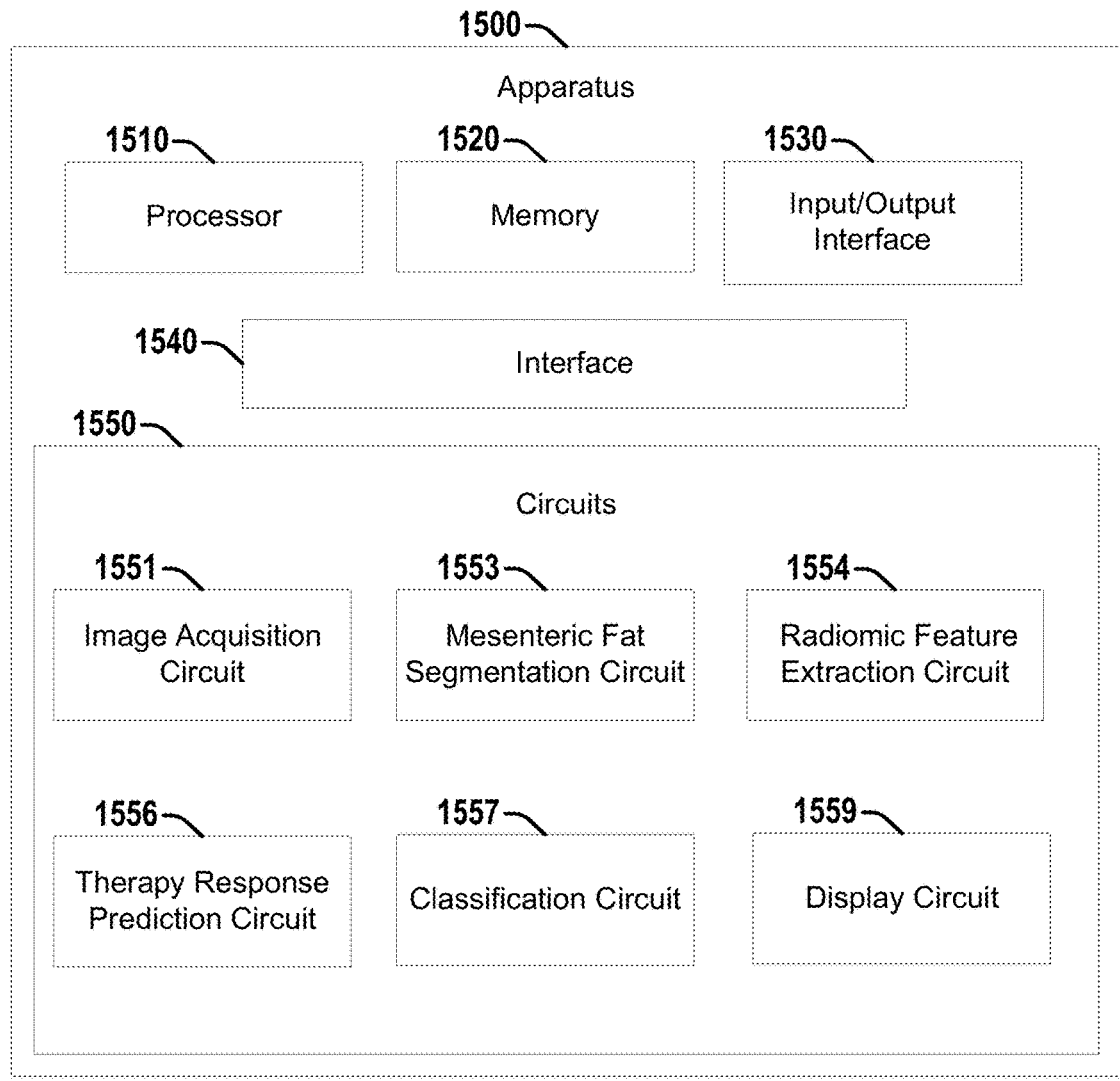
FIG. 15 illustrates a diagram of a first example apparatus that can facilitate identifying patients who will or will not respond to therapy for Crohn's disease according to various embodiments discussed herein.

Referring to FIG. 15, illustrated is a diagram of a first example apparatus 1500 that can facilitate predicting patient response to Crohn's disease therapy according to various embodiments discussed herein. Apparatus 1500 can be configured to perform various techniques discussed herein, including but not limited to, for example, operations 100, 200, 300, 400, or 1700. Apparatus 1500 includes a processor 1510. Apparatus 1500 also includes a memory 1520. Processor 1510 can, in various embodiments, include circuitry such as, but not limited to, one or more single-core or multi-core processors. Processor 1510 can include any combination of general-purpose processors and dedicated processors (e.g., graphics processors, application processors, etc.). The processor(s) can be coupled with and/or can comprise memory (e.g., memory 1520) or storage and can be configured to execute instructions stored in the memory 1520 or storage to enable various apparatus, applications, or operating systems to perform operations and/or methods discussed herein. Memory 1520 can be configured to store one or more radiological images, including an MRE study, or MRI, CT, PET, SPECT, or other types of medical imagery associated with a patient or patients. Each of the radiological image(s) can have a plurality of voxels, each voxel having an associated intensity. In some embodiments, memory 1520 can store a plurality of MRE studies of a population of patients demonstrating Crohn's disease, while in the same or other embodiments, memory 1520 can store a radiological image or diagnostic or prognostic MRE study of a patient demonstrating Crohn's disease for whom a probability of response or non-response is to be determined. Memory 1520 can be further configured to store metadata or one or more clinical features associated with the patient.

Apparatus 1500 also comprises an input/output (I/O) interface 1530, for example, associated with one or more I/O devices, a set of circuits 1550, and an interface 1540 that connects the processor 1510, the memory 1520, the I/O interface 1530, and the set of circuits 1550. I/O interface 1530 can be configured to transfer data between memory 1520, processor 1510, circuits 1550, and external devices, for example, a medical imaging device such as an MRI system or MRE system or apparatus.

The set of circuits 1550 may include an image acquisition circuit 1551, a mesenteric fat segmentation circuit 1553, a radiomic feature extraction circuit 1554, a therapy response prediction circuit 1556, a classification circuit 1557, and a display circuit 1559. Image acquisition circuit 1551 is configured to access one or more radiological images, including, for example, a plurality of MRE studies of a population of patients demonstrating Crohn's disease, or a diagnostic or prognostic MRE study of a patient demonstrating Crohn's disease for whom a probability of response or non-response to therapy is to be determined. Accessing the radiological image(s) can comprise accessing radiological image(s) stored in memory 1520. In one embodiment, accessing the radiological image(s) can include accessing radiological image(s) stored in a data storage device, including a hard disk drive, a solid-state device, a tape drive, or accessing radiological image(s) over a local area network. In one embodiment, the radiological image is a magnetic resonance enterography (MRE) study of a region of tissue demonstrating Crohn's disease, where the MRE study is acquired axial to the patient, where the MRE study includes a plurality of MRI images, where an MRI image includes a plurality of voxels, where each voxel of the plurality of voxels has an associated intensity. In one embodiment, the plurality of MRI images includes a non-fat-suppressed T2w sequence, and a fat-suppressed T2w sequence. Accessing the radiological image(s) can comprise acquiring electronic data, reading from a computer file, receiving a computer file, reading from a computer memory, or other computerized activity not practically performed in the human mind.

In one embodiment, a first member of the plurality of MRI images may be acquired according to a first MRI sequence, while a second, different member of the plurality of MRI images may be acquired according to a second, different MRI sequence, while a third, different member of the plurality of MRI images may be acquired according to a third, different MRI sequence. For example, in one embodiment, the MRE study includes an axial HASTE MRI image, and an axial HASTE SPAIR MRI image, where the axial HASTE MRI image, and the axial HASTE SPAIR MRI image, each includes a plurality of associated voxels, a voxel having an intensity. In another embodiment, the MRE study includes an axial HASTE MRI image, an axial HASTE SPAIR MRI image, a TruFI MRI image, and a TruFISP MRI image, where the axial HASTE MRI image, the axial HASTE SPAIR MRI image, the TruFI MRI image, and the TruFISP MRI image each includes a plurality of associated voxels, a voxel having an intensity.

Mesenteric fat segmentation circuit 1553 is configured to define a mesenteric fat region by segmenting mesenteric fat represented in the radiological image. In one embodiment, mesenteric fat segmentation circuit 1553 is configured to define a mesenteric fat region by defining a VAT region by segmenting VAT represented in the radiological image; defining an SQF region by segmenting SQF represented in the radiological image; and defining the mesenteric fat region by segmenting mesenteric fat represented in the radiological image based on the VAT region, the SQF region, and a proximity to a bowel wall represented in the radiological image. The proximity may, in one embodiment, be five (5) pixels. In embodiments described herein, the proximity may be user-adjustable. The proximity may be adjustable based, for example, on image resolution, available computational resources, or other criteria. Mesenteric fat segmentation circuit 1553 may be configured to define the mesenteric fat region according to various techniques described herein, including, for example, operations 400. For example, mesenteric fat segmentation circuit 1553 may be configured to define the mesenteric fat region using pre-processing that includes correction and filtering as described herein.

Radiomic feature extraction circuit 1554 is configured to extract a set of radiomic features from the mesenteric fat region. In one embodiment, the set of radiomic features includes at least three radiomic features. In one embodiment, the patient is a pediatric Crohn's disease patient, and the set of radiomic features includes a Gabor feature, a Haralick inverse difference moment feature, and a Haralick inertia feature. In another embodiment, the patient is an adult Crohn's disease patient, and the set of radiomic features includes a Laws feature, a Haralick inertia feature, and a Haralick inverse difference moment feature. In another embodiment, the set of radiomic features may include another, different number of radiomic features.

Therapy response prediction circuit 1556 is configured to compute a probability of response to Crohn's disease therapy based, at least in part, on the set of radiomic features. In one embodiment, therapy response prediction circuit 1556 is configured to compute the probability using a QDA machine learning approach. For example, in one embodiment, therapy response prediction circuit 1556 is configured as a QDA classifier. In another embodiment, therapy response prediction circuit 1556 may be configured to compute the probability using another, different machine learning technique. For example, therapy response prediction circuit 1556 may be configured as an LDA classifier, a DLDA classifier, an SVM classifier, an RF classifier, or may be configured as a deep learning classifier, including, for example, as a CNN. In one embodiment, therapy response prediction circuit 1556 may be configured to compute the probability as a value within the range [0, 1].

Classification circuit 1557 is configured to classify the patient as a responder or non-responder based, at least in part, on the probability. For example, classification circuit 1557 may classify a patient having an associated probability of 1 as a responder, and may classify a different patient having an associated probability of 0, as a non-responder. Other classification schemes may be employed. For example, a patient having an associated probability of <=0.5 may be classified as a non-responder, while a patient having an associated probability of >0.5 may be classified as a responder.

Display circuit 1559 is configured to display the classification according to various techniques described herein. Display circuit 1559 may be further configured to optionally display at least one of the probability, the mesenteric fat region, the VAT region, the SQF region, the set of radiomic features, or one or more radiological images associated with the patient.

Figure 16:
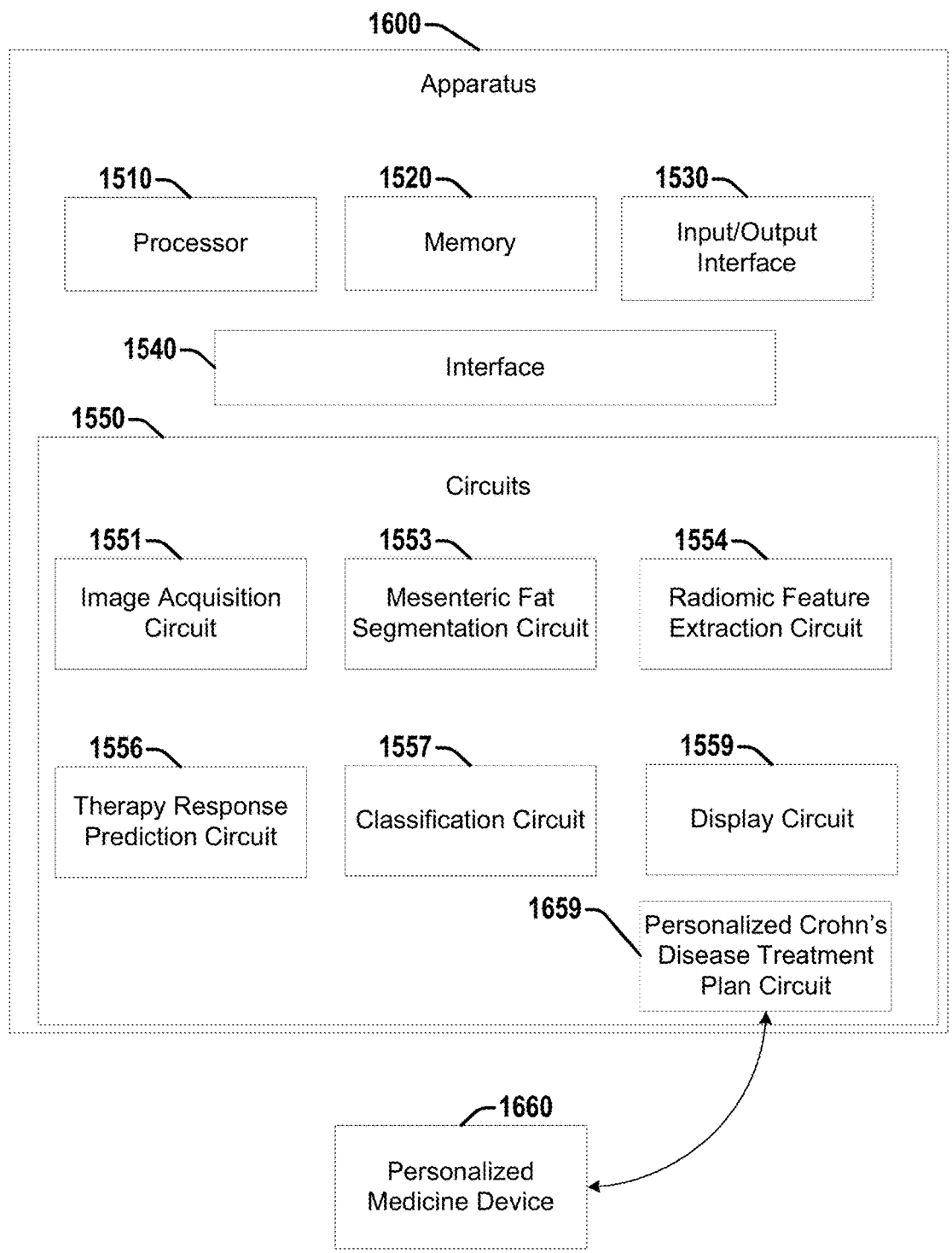
FIG. 16 illustrates a diagram of a second example apparatus that can facilitate identifying patients who will or will not respond to therapy for Crohn's disease according to various embodiments discussed herein.

Referring to FIG. 16, illustrated is a diagram of a second example apparatus 1600 that can facilitate predicting patient response to Crohn's disease therapy according to various embodiments discussed herein. Example apparatus 1600 is similar to apparatus 1500, including elements 1510-1559, but includes additional details and elements. Apparatus 1600 includes personalized Crohn's disease treatment plan circuit 1659.

Personalized Crohn's disease treatment plan circuit 1659 may be configured to generate a personalized Crohn's disease treatment plan based, at least in part, on a probability obtained from therapy response classification circuit 1556, or a classification obtained from classification circuit 1557. Personalized Crohn's disease treatment plan circuit 1659 can be configured to generate a personalized Crohn's disease treatment plan for the patient of whom the MRE study was acquired based, at least in part, on the probability or classification derived therefrom. Defining a personalized Crohn's disease treatment plan facilitates delivering a particular treatment that will be therapeutically active to the patient, while minimizing negative or adverse effects experienced by the patient. For example, the personalized Crohn's disease treatment plan may suggest a first surgical treatment, may suggest a first pharmaceutical agent dosage or schedule, and/or other treatments for a patient determined to likely experience response to Crohn's disease therapy, while the personalized Crohn's disease treatment plan may suggest a second, different surgical treatment, a second different pharmaceutical agent dosage or schedule, to a patient determined to be unlikely to respond to Crohn's disease therapy.

Apparatus 1600 can further include personalized medicine device 1660. Apparatus 1600 can be configured to provide the probability, classification, radiological image, personalized Crohn's disease treatment plan, or other data to personalized medicine device 1660. Personalized medicine device 1660 may be, for example, a computer assisted diagnosis (CADx) system or other type of personalized medicine device that can be used to facilitate the prediction of response to therapy in Crohn's disease as described herein. In one embodiment, personalized Crohn's disease treatment plan circuit 1659 can control personalized medicine device 1660 to display the classification, the probability, the personalized Crohn's disease treatment plan, or other data on a computer monitor, a smartphone display, a tablet display, or other displays.

Figure 17:
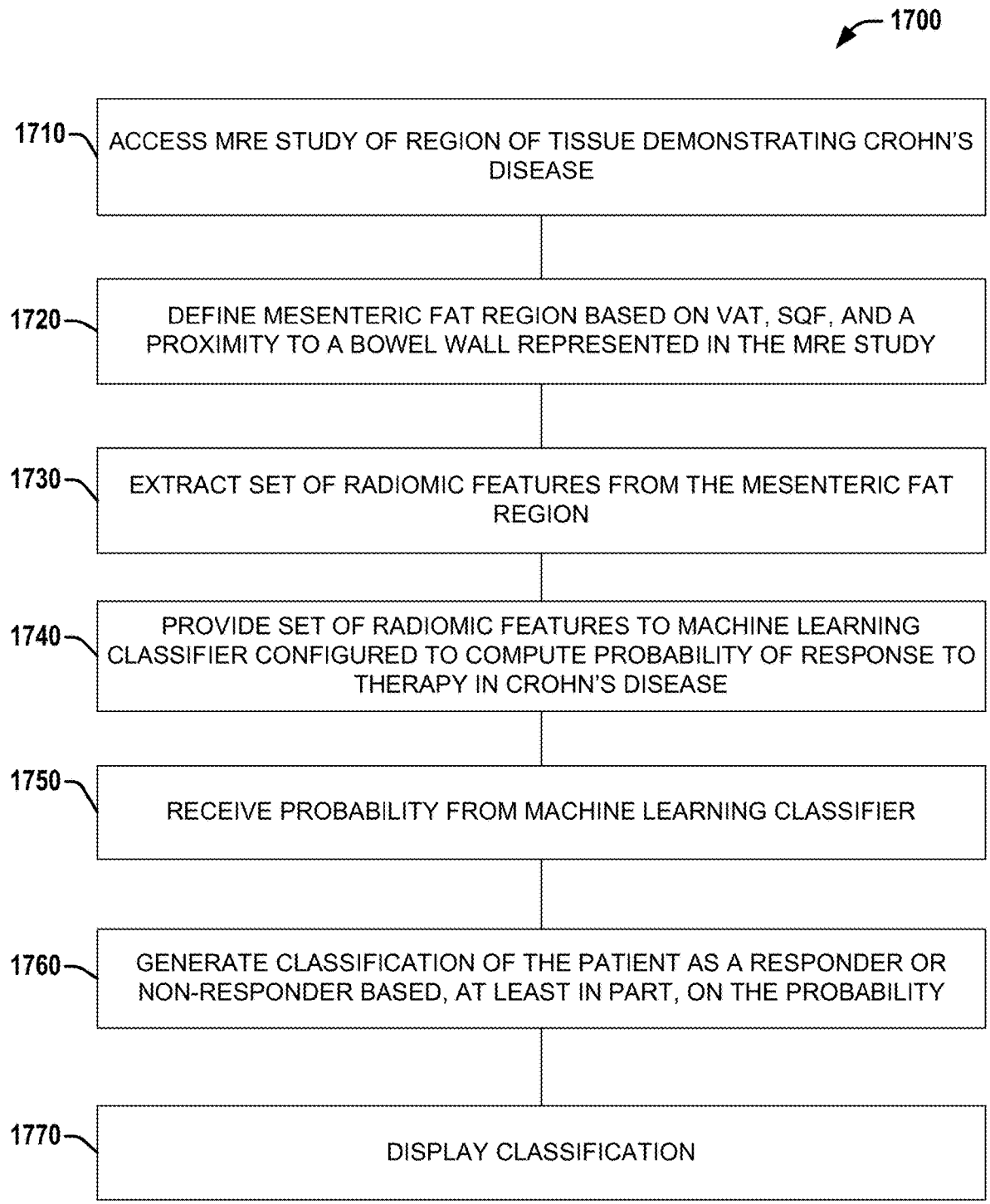
FIG. 17 illustrates a diagram of an example flow of a method or set of operations that classifies a patient who will or will not respond to therapy for Crohn's disease according to various embodiments discussed herein.

FIG. 17 illustrates a diagram of an example flow of a method or set of operations 1700 that facilitates computation of a probability of response versus non-response in a patient demonstrating Crohn's disease. Operations 1700 includes, at 1710, accessing a magnetic resonance enterography (MRE) study of a region of tissue demonstrating Crohn's disease associated with a patient. The MRE study is acquired axial to the patient. The MRE study includes a plurality of MRI images, where an MRI image includes a plurality of voxels, where each voxel of the plurality of voxels has an associated intensity. Accessing the MRE study includes acquiring electronic data, reading from a computer file, receiving a computer file, reading from a computer memory, or other computerized activity not practically performed in the human mind.

Operations 1700 also includes, at 1720, defining a mesenteric fat region. Defining the mesenteric fat region, in one embodiment, includes segmenting a visceral adipose fat (VAT) region represented in the MRE study, segmenting a subcutaneous fat (SQF) represented in the MRE study, and segmenting mesenteric fat represented in the MRE study based on the VAT region, SQF region, and a proximity to a bowel wall represented in the MRE study. The proximity may be, for example, five pixels. Defining the mesenteric fat region includes acquiring electronic data, reading from a computer file, receiving a computer file, reading from a computer memory, or other computerized activity not practically performed in the human mind.

Operations 1700 also includes, at 1730, extracting a set of radiomic features from the mesenteric fat region. In one embodiment, the set of radiomic features includes at least one of a Gabor feature, a Haralick inverse difference moment feature, a Haralick inertia feature, or a Laws feature. Extracting the set of radiomic features includes acquiring electronic data, reading from a computer file, receiving a computer file, reading from a computer memory, or other computerized activity not practically performed in the human mind.

Operations 1700 also includes, at 1740, providing the set of radiomic features to a machine learning classifier. The machine learning classifier is configured to compute a probability of response to therapy in Crohn's disease based, at least in part, on the set of radiomic features. In one embodiment, the machine learning classifier is a QDA classifier. Providing the set of radiomic features to the machine learning classifier includes acquiring electronic data, reading from a computer file, receiving a computer file, reading from a computer memory, or other computerized activity not practically performed in the human mind.

Operations 1700 also includes, at 1750, receiving, from the machine learning classifier, a probability that the region of tissue will respond to therapy. Receiving the probability includes acquiring electronic data, reading from a computer file, receiving a computer file, reading from a computer memory, or other computerized activity not practically performed in the human mind.

Operations 1700 also includes, at 1760, generating a classification of the patient as a responder or non-responder based, at least in part, on the probability, according to various techniques described herein. Generating the classification includes acquiring electronic data, reading from a computer file, receiving a computer file, reading from a computer memory, or other computerized activity not practically performed in the human mind.

Operations 1700 further includes, at 1770, displaying the classification according to various techniques described herein. In one embodiment, displaying the classification may also include optionally displaying the probability, the set of radiomic features or values associated with the set of radiomic features, the mesenteric fat region, or the MRE study. Displaying the classification includes acquiring electronic data, reading from a computer file, receiving a computer file, reading from a computer memory, or other computerized activity not practically performed in the human mind.

In various embodiments, the probability may be computed using a machine learning classifier. For example, a machine learning classifier may be trained to distinguish a patient demonstrating Crohn's disease likely to experience response to therapy from a patient demonstrating Crohn's disease unlikely to experience response based on a baseline, pre-treatment diagnostic MRE study associated with the patient. In this embodiment, training the machine learning classifier may include accessing a training dataset of MRE studies of patients demonstrating Crohn's disease. Each MRE study may include a plurality of MRI images, for example, a Gd-T1w MRI image, a T2w MRI image, and a FLAIR MRI image, that can comprise a plurality of voxels, where each voxel can have an associated intensity. The training dataset can comprise both a positive training set of MRE studies and a negative training set of MRE studies in connection with a given medical condition (e.g., Crohn's disease). The positive training set can comprise MRE studies that have features (e.g., one or more features that have been determined to be predictively significant specifically in connection with the given medical condition, etc.) that are predictive of an outcome (e.g., response, non-response) of the given medical condition (e.g., Crohn's disease). The negative training set can comprise images of samples that are irrelevant, have non-predictive patterns (e.g., non-lesion regions), have artifacts, or are non-diagnostic tissue.

Training the machine learning classifier may include accessing a training dataset of MRE studies of a patients demonstrating Crohn's disease, and a testing set of MRE studies of patients demonstrating Crohn's disease. The training dataset and the testing dataset of MRE studies are acquired from a population of patients that experienced pathologically proven Crohn's disease as described herein. Members of the population experienced either response or non-response. Training the machine learning classifier may include training the machine learning classifier until a threshold level of accuracy is achieved, until a threshold time has been spent training the machine learning classifier, until a threshold amount of computational resources have been expended training the machine learning classifier, or until a user terminates training. Other training termination conditions may be employed. Training the machine learning classifier may also include determining which features of members of the training dataset or testing dataset are most discriminative in distinguishing patients likely to experience response from patients unlikely to experience response. Training the machine learning classifier may also include determining settings outside the classifier architecture but relevant to its learning behavior. FIG. 3 illustrates one example set of operations 300 suitable for training a machine learning classifier according to embodiments described herein. Embodiments may further display operating parameters or characteristics of the machine learning classifier, during both training and testing, or during clinical operation.

Examples herein can include subject matter such as an apparatus, a personalized medicine system, a CADx system, an MRE or MRI system, a processor, a system, circuitry, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or operations or of an apparatus or system for predicting response to therapy in Crohn's disease, or the determination of a probability of a patient experiencing responding or not responding to therapy in Crohn's disease, or analyzing the severity of Crohn's disease, according to embodiments and examples described herein.

Example 1 is a non-transitory computer-readable device storing computer-executable instructions that, when executed, cause a processor to perform operations, comprising: accessing a radiological image of a region of tissue demonstrating Crohn's disease, where the radiological image includes a plurality of pixels, a pixel having an intensity, where the radiological image is associated with a patient; defining a mesenteric fat region by segmenting mesenteric fat represented in the radiological image; extracting a set of radiomic features from the mesenteric fat region; providing the set of radiomic features to a machine learning classifier configured to compute a probability of response to therapy in Crohn's disease based, at least in part, on the set of radiomic features; receiving, from the machine learning classifier, a probability that the region of tissue will respond to therapy; generating a classification of the patient as a responder or non-responder based, at least in part, on the probability; and displaying the classification.

Example 2 comprises the subject matter of any variation of any of example 1, where the radiological image is a magnetic resonance enterography (MRE) image.

Example 3 comprises the subject matter of any variation of any of example(s) 1-2, where the MRE image includes a non-fat-suppressed T2w sequence and a fat-suppressed T2w sequence, where the MRE image is acquired axial to the patient.

Example 4 comprises the subject matter of any variation of any of example(s) 1-3, where defining the mesenteric fat region comprises: defining a VAT region by segmenting VAT represented in the radiological image; defining a subcutaneous fat (SQF) region by segmenting SQF represented in the radiological image; and defining the mesenteric fat region by segmenting mesenteric fat represented in the radiological image based on the VAT region, SQF region, and a proximity to a bowel wall represented in the radiological image.

Example 5 comprises the subject matter of any variation of any of example(s) 1-4, where the patient is a pediatric Crohn's disease patient.

Example 6 comprises the subject matter of any variation of any of example(s) 1-5, where the set of radiomic features includes a Gabor feature, a Haralick inverse difference moment feature, and a Haralick inertia feature.

Example 7 comprises the subject matter of any variation of any of example(s) 1-6, where the patient is an adult Crohn's disease patient.

Example 8 comprises the subject matter of any variation of any of example(s) 1-7, where the set of radiomic features includes a Laws feature, a Haralick inertia feature, and a Haralick inverse difference moment feature.

Example 9 comprises the subject matter of any variation of any of example(s) 1-8, where the machine learning classifier is a quadratic discriminant analysis (QDA) classifier, a linear discriminant analysis (LDA) classifier, a random forest (RF) classifier, or a convolutional neural network (CNN) classifier.

Example 10 comprises the subject matter of any variation of any of example(s) 1-9, the operations further comprising training the machine learning classifier to compute the probability of response to therapy in Crohn's disease based, at least in part, on the set of radiomic features.

Example 11 comprises the subject matter of any variation of any of example(s) 1-10, the operations further comprising generating a personalized Crohn's disease treatment plan based, at least in part, on the classification; and optionally displaying the personalized Crohn's disease treatment plan.

Example 12 comprises an apparatus comprising: a processor; a memory configured to store a radiological image of a region of tissue demonstrating Crohn's disease, where the radiological image includes a plurality of pixels, where each pixel of the plurality of pixels has an associated intensity, where the radiological image is associated with a patient; an input/output (I/O) interface; a set of circuits; and an interface that connects the processor, the memory, the I/O interface, and the set of circuits, the set of circuits comprising: an image acquisition circuit configured to access a radiological image associated with a patient; a mesenteric fat segmentation circuit configured to define a mesenteric fat region by segmenting mesenteric fat represented in the radiological image; a radiomic feature extraction circuit configured to extract a set of radiomic features from the mesenteric fat region, where the set of radiomic features includes at least three radiomic features; a therapy response prediction circuit configured to compute a probability of response to Crohn's disease therapy based, at least in part, on the set of radiomic features; a classification circuit configured to classify the patient as a responder or non-responder based, at least in part, on the probability; and a display circuit configured to display the classification.

Example 13 comprises the subject matter of any variation of any of example(s) 12, where the radiological image is a magnetic resonance enterography (MRE) study of a region of tissue demonstrating Crohn's disease, where the MRE study is acquired axial to the patient, where the MRE study includes a plurality of MRI images, where an MRI image includes a plurality of voxels, wherein each voxel of the plurality of voxels has an associated intensity.

Example 14 comprises the subject matter of any variation of any of example(s) 12-13, where the plurality of MRI images includes a non-fat-suppressed T2w sequence and a fat-suppressed T2w sequence.

Example 15 comprises the subject matter of any variation of any of example(s) 12-14, where the mesenteric fat segmentation circuit is configured to define the mesenteric fat region by: defining a visceral adipose tissue (VAT) region by segmenting VAT represented in the radiological image; defining a subcutaneous fat (SQF) region by segmenting SQF represented in the radiological image; and defining the mesenteric fat region by segmenting mesenteric fat represented in the radiological image based on the VAT region, the SQF region, and a proximity to a bowel wall represented in the radiological image.

Example 16 comprises the subject matter of any variation of any of example(s) 12-15, where the patient is a pediatric Crohn's disease patient, and where the set of radiomic features includes a Gabor feature, a Haralick inverse difference moment feature, and a Haralick inertia feature.

Example 17 comprises the subject matter of any variation of any of example(s) 12-16, where the patient is an adult Crohn's disease patient, and where the set of radiomic features includes a Laws feature, a Haralick inertia feature, and a Haralick inverse difference moment feature.

Example 18 comprises the subject matter of any variation of any of example(s) 12-17, where the therapy response prediction circuit is configured to compute the probability using a quadratic discriminant analysis (QDA) machine learning approach.

Example 19 comprises the subject matter of any variation of any of example(s) 12-13, the set of circuits further comprising a personalized Crohn's disease treatment plan circuit configured to: generate a personalized Crohn's disease treatment plan associated with the patient based, at least in part, on the classification; and optionally control the display circuit to display the personalized Crohn's disease treatment plan.

Example 20 is a non-transitory computer-readable medium storing computer-executable instructions that, when executed, cause a processor to perform operations, comprising: accessing a magnetic resonance enterography (MRE) study of a region of tissue demonstrating Crohn's disease associated with a patient, where the MRE study is acquired axial to the patient, where the MRE study includes a plurality of MRI images, where an MRI image includes a plurality of voxels, wherein each voxel of the plurality of voxels has an associated intensity; defining a mesenteric fat region by segmenting a visceral adipose fat (VAT) region represented in the MRE study, segmenting a subcutaneous fat (SQF) region represented in the MRE study, and segmenting mesenteric fat represented in the MRE study based on the VAT region, SQF region, and a proximity to a bowel wall represented in the MRE study; extracting a set of radiomic features from the mesenteric fat region, where the set of radiomic features includes at least one of a Gabor feature, a Haralick inverse difference moment feature, a Haralick inertia feature, or a Laws feature; providing the set of radiomic features to a machine learning classifier configured to compute a probability of response to therapy in Crohn's disease based, at least in part, on the set of radiomic features; receiving, from the machine learning classifier, a probability that the region of tissue will respond to therapy; generating a classification of the patient as a responder or non-responder based, at least in part, on the probability; and displaying the classification.

Example 21 comprises an apparatus comprising means for executing any of the described operations of examples 1-20.

Example 22 comprises a machine readable medium that stores instructions for execution by a processor to perform any of the described operations of examples 1-20.

Example 23 comprises an apparatus comprising: a memory; and one or more processors configured to: perform any of the described operations of examples 1-20.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable storage device storing computer-executable instructions that, when executed, cause a processor to perform operations, the operations comprising:
  accessing a radiological image of a region of tissue demonstrating Crohn's disease, where the radiological image includes a plurality of pixels, a pixel having an intensity, where the radiological image is associated with a patient;
  defining a mesenteric fat region by segmenting mesenteric fat represented in the radiological image;
  extracting a set of radiomic features from the mesenteric fat region;
  providing the set of radiomic features to a machine learning classifier configured to compute a probability of response to therapy in Crohn's disease based, at least
in part, on the set of radiomic features;
receiving, from the machine learning classifier, a probability that the region of tissue will respond to therapy;
generating a classification of the patient as a responder or non-responder based, at least in part, on the probability; and
displaying the classification.

2. The non-transitory computer-readable storage device of claim 1, where the radiological image is a magnetic resonance enterography (MRE) image.

3. The non-transitory computer-readable storage device of claim 2,
where the MRE image includes a non-fat-suppressed T2w sequence and a fat-suppressed T2w sequence, where the MRE image is acquired axial to the patient; and
where the mesenteric fat region is defined using both the non-fat-suppressed T2w sequence and the fat-suppressed T2w sequence.

4. The non-transitory computer-readable storage device of claim 3 where defining the mesenteric fat region comprises:
defining a visceral adipose tissue (VAT) region by segmenting VAT represented in the radiological image;
defining a subcutaneous fat (SQF) region by segmenting SQF represented in the radiological image; and
defining the mesenteric fat region by segmenting mesenteric fat represented in the radiological image based on the VAT region, the SQF region, and a proximity to a bowel wall represented in the radiological image.

5. The non-transitory computer-readable storage device of claim 3, where defining the mesenteric fat region comprises:
utilizing the fat-suppressed T2w sequence to produce an intestine mask;
masking the MRE image using the intestine mask to identify fat regions of the MRE image;
disconnecting visceral fat tissue (VAT) regions and subcutaneous fat (SQF) regions of the identified fat regions; and
obtaining the mesenteric fat region from the VAT regions.

6. The non-transitory computer-readable storage device of claim 5, where the set of radiomic features includes a Gabor feature, a Haralick inverse difference moment feature, and a Haralick inertia feature.

7. The non-transitory computer-readable storage device of claim 1, where the patient is an adult Crohn's disease patient.

8. The non-transitory computer-readable storage device of claim 7, where the set of radiomic features includes a Laws feature, a Haralick inertia feature, and a Haralick inverse difference moment feature.

9. The non-transitory computer-readable storage device of claim 1, where the machine learning classifier is a quadratic discriminant analysis (QDA) classifier, a linear discriminant analysis (LDA) classifier, a random forest (RF) classifier, or a convolutional neural network (CNN) classifier.

10. The non-transitory computer-readable storage device of claim 9, the operations further comprising training the machine learning classifier to compute the probability of response to therapy in Crohn's disease based, at least in part, on the set of radiomic features.

11. An apparatus comprising:
a processor;
a memory configured to store a radiological image of a region of tissue demonstrating Crohn's disease, where the radiological image includes a plurality of pixels, where each pixel of the plurality of pixels has an associated intensity, where the radiological image is associated with a patient;
an input/output (I/O) interface;
a set of circuits; and
an interface that connects the processor, the memory, the I/O interface, and the set of circuits, the set of circuits comprising:
an image acquisition circuit configured to access the radiological image associated with the patient;
a mesenteric fat segmentation circuit configured to define a mesenteric fat region by segmenting mesenteric fat represented in the radiological image;
a radiomic feature extraction circuit configured to extract a set of radiomic features from the mesenteric fat region, where the set of radiomic features includes at least three radiomic features;
a therapy response prediction circuit configured to compute a probability of response to Crohn's disease therapy based, at least in part, on the set of radiomic features;
a classification circuit configured to classify the patient as a responder or non-responder based, at least in part, on the probability; and
a display circuit configured to display the classification.

12. The apparatus of claim 11, where the radiological image is a magnetic resonance enterography (MRE) study of the region of tissue demonstrating Crohn's disease, where the MRE study is acquired axial to the patient, where the MRE study includes a plurality of MRI images, where an MRI image includes a plurality of voxels, wherein each voxel of the plurality of voxels has an associated intensity.

13. The apparatus of claim 12, where the plurality of MRI images includes a non-fat-suppressed T2w sequence and a fat-suppressed T2w sequence.

14. The apparatus of claim 11, where the mesenteric fat segmentation circuit is configured to define the mesenteric fat region by:
defining a visceral adipose tissue (VAT) region by segmenting VAT represented in the radiological image;
defining a subcutaneous fat (SQF) region by segmenting SQF represented in the radiological image; and
defining the mesenteric fat region by segmenting mesenteric fat represented in the radiological image based on the VAT region, the SQF region, and a proximity to a bowel wall represented in the radiological image.

15. The apparatus of claim 11, where the patient is a pediatric Crohn's disease patient, and where the set of radiomic features includes a Gabor feature, a Haralick inverse difference moment feature, and a Haralick inertia feature.

16. The apparatus of claim 11, the set of circuits further comprising a personalized Crohn's disease treatment plan circuit configured to:
generate a personalized Crohn's disease treatment plan associated with the patient based, at least in part, on the classification; and
optionally control the display circuit to display the personalized Crohn's disease treatment plan.

17. A non-transitory computer-readable medium storing computer-executable instructions that, when executed, cause a processor to perform operations, comprising:
accessing a magnetic resonance enterography (MRE) study of a region of tissue demonstrating Crohn's disease associated with a patient, where the MRE study is acquired axial to the patient, where the MRE study includes a plurality of MRI images, where an MRI image includes a plurality of voxels, wherein each voxel of the plurality of voxels has an associated intensity;

defining a mesenteric fat region in the MRE study;

extracting a set of radiomic features from the mesenteric fat region, where the set of radiomic features includes at least one of a Gabor feature, a Haralick inverse difference moment feature, a Haralick inertia feature, or a Laws feature;

providing the set of radiomic features to a machine learning classifier configured to compute a probability of response to therapy in Crohn's disease based, at least in part, on the set of radiomic features;

receiving, from the machine learning classifier, a probability that the region of tissue will respond to therapy;

generating a classification of the patient as a responder or non-responder based, at least in part, on the probability; and displaying the classification.

18. The apparatus of claim 13, where defining the mesenteric fat region comprises:

utilizing the fat-suppressed T2w sequence to produce an intestine mask;

masking the radiological image using the intestine mask to identify fat regions of the radiological image;

eroding the fat regions of the radiological image to identify visceral fat tissue (VAT) regions and subcutaneous fat (SQF) regions; and obtaining the mesenteric fat region from the VAT regions.

19. The non-transitory computer-readable medium of claim 17, further comprising:

defining the mesenteric fat region by segmenting a visceral adipose fat (VAT) region represented in the MRE study, segmenting a subcutaneous fat (SQF) region represented in the MRE study, and segmenting mesenteric fat represented in the MRE study based on the VAT region, SQF region, and a proximity to a bowel wall represented in the MRE study.

20. The non-transitory computer-readable medium of claim 17, wherein the plurality of MRI images include a non-fat-suppressed sequence and a fat-suppressed sequence; and wherein defining the mesenteric fat region comprises:

utilizing the fat-suppressed sequence to produce an intestine mask;

masking the radiological image using the intestine mask to identify fat regions of the MRE study;

disconnecting visceral fat tissue (VAT) regions and subcutaneous fat (SQF) regions of the identified fat regions; and obtaining the mesenteric fat region from the VAT regions.

* * * * *